US012324814B2

(12) United States Patent
Jiang et al.

(10) Patent No.: US 12,324,814 B2
(45) Date of Patent: Jun. 10, 2025

(54) MANGANESE COMPOSITION FOR ENHANCING IMMUNITY

(71) Applicant: PEKING UNIVERSITY, Beijing (CN)

(72) Inventors: Zhengfan Jiang, Beijing (CN); Chenguang Wang, Beijing (CN); Rui Zhang, Beijing (CN); Mengze Lv, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 836 days.

(21) Appl. No.: 17/594,468

(22) PCT Filed: Apr. 20, 2020

(86) PCT No.: PCT/CN2020/085507
§ 371 (c)(1),
(2) Date: Oct. 18, 2021

(87) PCT Pub. No.: WO2020/211857
PCT Pub. Date: Oct. 22, 2020

(65) Prior Publication Data
US 2022/0193125 A1 Jun. 23, 2022

(30) Foreign Application Priority Data
Apr. 19, 2019 (CN) .......................... 201910319344.1

(51) Int. Cl.
A61K 33/32 (2006.01)
A61P 19/00 (2006.01)
A61P 31/12 (2006.01)

(52) U.S. Cl.
CPC .............. A61K 33/32 (2013.01); A61P 19/00 (2018.01); A61P 31/12 (2018.01)

(58) Field of Classification Search
None
See application file for complete search history.

(56) References Cited

U.S. PATENT DOCUMENTS

| 2,031,579 | A | * | 2/1936 | Booth ................... C01B 25/377 423/52 |
| 4,720,386 | A | | 1/1988 | McCollester |
| 2004/0131650 | A1 | * | 7/2004 | Trouve ................. A61K 9/0019 424/401 |
| 2004/0219361 | A1 | | 11/2004 | Cui et al. |
| 2010/0015636 | A1 | | 1/2010 | Charlton |

FOREIGN PATENT DOCUMENTS

| CN | 1542449 | 11/2004 |
| CN | 101151532 | 3/2008 |
| CN | 101225092 | 7/2008 |
| CN | 102515276 | 6/2012 |
| CN | 107412260 | 12/2017 |
| CN | 107456575 | 12/2017 |
| JP | 2004/527615 | 9/2004 |
| WO | WO 02/080840 | 10/2002 |
| WO | WO 2004/060284 | 7/2004 |

OTHER PUBLICATIONS

Office Communication issued in correspondence Japanese Application No. 2021-561978 dated Nov. 30, 2022 {English translation}.
Slanetz et al., "Autologous Anticancer Antigen Preparation for Specific Immunotherapy in Advanced Cancer Patients" Cancer Immunol Immunother, 13: 75-84, 1982.
Supplemental European Search Report issued in European Application No. 20791542.2, Dec. 21, 2022.
Akira and Takeda, "Toll-like receptor signalling," Nature Reviews Immunology, 4:499-511, 2004.
Ben-Sasson et al., "IL-1 acts directly on CD4 T cells to enhance their antigen-driven expansion and differentiation," PNAS, 106(17):7119-7124, 2009.
Blaauboer et al., "MPYS/STING-Mediated TNF-α, Not Type I IFN, Is Essential for the Mucosal Adjuvant Activity of (3'-5')-Cyclic-Di-Guanosine-Monophosphate In Vivo," J. Immunol., 192(1):492-502, 2014.
Bruns and Horvath, "Activation of RIG-I-like receptor signal transduction," Critical Reviews in Biochemistry and Molecular Biology,47(2):194-206, 2012.
Carroll et al., "The Vaccine Adjuvant Chitosan Promotes Cellular Immunity via DNA Sensor cGAS-STING-Dependent Induction of Type I Interferons," Immunity, 44(3):597-608, 2016.
Eisenbarth et al., "Crucial role for the Nalp3 inflammasome in the immunostimulatory properties of aluminium adjuvants," Nature, 453(7198):1122-1126, 2008.
English translation of International Search Report issued in International Patent Application No. PCT/CN2020/085507, dated Jul. 22, 2020.
Ivashikiv and Donlin, "Regulation of type I interferon responses," Nat. Rev. Immunol., 14(1):36-49, 2014.
Jiang et al., "CD14 is required for MyD88-independent LPS signaling," Nature Immunology, 6(6):565-570, 2005.
Kool et al., "Cutting Edge: Alum Adjuvant Stimulates Inflammtory Dendritic Cells through Activation fo the NALP3 Inflammasome," J. Immunol., 181:3755-3759, 2008.
Li et al., "Cutting Edge: Inflammasome activation by the Alum and Alum's adjuvant effect are mediated by NLRP3," J. Immunol., 181(1):17-21, 2008.
Li et al., "Pivotal Roles of cGAS-cGAMP Signaling in Antiviral Defense and Immune Adjuvant Effects," Science, 341(6152), 10 pages, 2013.
Longhi et al., "Dendritic cells require a systemic type I interferon responds to mature and induce CD4+Th1 immunity with poly IC as adjuvant," J. Exp. Med., 206(7):1589-1602, 2009.
Ma and Damania, "The cGAS-STING defense pathway and Its Counteaction by Viruses," Cell Host & Microbe, 19:150-158, 2016.

(Continued)

Primary Examiner — Nicole P Babson
(74) Attorney, Agent, or Firm — Parker Highlander PLLC

(57) ABSTRACT

An immune enhancement composition and a vaccine composition comprising newly precipitated manganese and/or colloid manganese, a preparation method therefor, and use thereof for immunization and/or vaccination enhancement.

13 Claims, 19 Drawing Sheets

(56) References Cited

OTHER PUBLICATIONS

Marrack et al., "Towards an understanding of the adjuvant action of aluminium," *Nat. Rev. Immunol.*, 9(4):287-293, 2009.
Nohynek et al., "AS03 Adjuvanted AH1N1 Vaccine Associated with an Abrupt Increase in the Incidence of Childhood Narcolepsy in Finland," *PLoS ONE*, 7(3):e33536, 9 pages, 2012.
Oleszycka et al., "IL-1α and inflammasome-independent IL-1β promote neutrophil infiltration following alum vaccination," *FEBS Journal*, 283:9-24, 2016.
Schneider et al., "Interferon-Stimulated Genes: A Complex Web of Host Defenses," *Annu. Rev. Immunol.*, 32:513-545, 2014.
Schroder and Tschopp, "The Inflammasomes," *Cell*, 140:921-832, 2010.
Tang et al., "The Chemotherapeutic Agent DMXAA as a Unique IRF3-Dependent Type-2 Vaccine Adjuvant," *PLoS ONE*, 8(3):e60038, 6 p. 2013.
Wang et al., "Manganese Increases the Sensitivity of the cGAS-STING Pathway for Double-Stranded DNA and Is Required for the Host Defense against DNA Viruses," *Immunity*, 48:675-687, 2018.
Wilson et al., "Inflammasome-dependent and -independent IL-18 production mediates immunity to the ISCOMATRIX adjuvant," *J. Immunol.*, 192:3259-3268, 2014.
Xia et al., "The mevalonate pathway is a druggable target for vaccine adjuvant discovery," *Cell*, 175:1059-1073, 2018.

\* cited by examiner

MANGANESE COMPOSITION FOR ENHANCING IMMUNITY

CROSS REFERENCE TO RELATED APPLICATIONS

This application is a national phase application under 35 U.S.C. § 371 of International Application No. PCT/CN2020/085507, filed Apr. 20, 2020, which claims the priority of Chinese Patent Application No. 201910319344.1, filed with the China National Intellectual Property Administration on Apr. 19, 2019, each of which is hereby incorporated by reference in entirety.

FIELD

The present disclosure provides divalent manganese colloid or newly precipitated divalent manganese for enhancing immunity, and uses thereof, which may be, for example, as immunoadjuvant, and for antiviral or antitumor applications.

BACKGROUND

The body protects itself from foreign pathogens through the innate immune system and the adaptive immune system. Innate immunity has a promoting effect on adaptive immunity. When the body is infected by a pathogen, it first initiates an innate immune response, recognizes the pathogen's pathogen-related molecular patterns through pattern recognition receptors, and activates a variety of signaling pathways, such as TLR pathway (1), RLR pathway (2), cGAS-STING pathway (3), inflammasome activation (4), etc. The activation of these pathways leads to the production of many downstream cytokines, including type I interferon, IL-1β, IL-18 and so on.

Type I interferon can activate the JAK-STAT pathway through autocrine and paracrine pathways, induce the expression of a large number of antiviral genes, and achieve the effect of resisting viral infections (5, 6). At the same time, type I interferon can promote the maturation of antigen-presenting cells (7). The antigen-presenting cells present pathogenic microorganisms or tumor antigens to T cells, and activate antigen-specific $CD4^+$ T cells and $CD8^+$ T cells; it can also promote B Cell activation to produce antigen-specific antibodies, and promotes the production of memory B cells and immune memory.

The pro-inflammatory factor IL-1β can directly act on $CD4^+$ T cells and promote the proliferation of T cells (8); IL-18 can effectively enhance Th1 immune response, and can also promote the proliferation and cytotoxicity of T cells and NK cells (9).

There are currently four adjuvants approved by the FDA for use on humans: aluminum adjuvants, MF59, AS03, and AS04. Aluminum adjuvants have been widely used since 1920 and are used in hepatitis A (HAV) vaccine, hepatitis B (HBV) vaccine, diphtheria-tetanus-pertussis (DTP) vaccine, human papillomavirus (HPV) vaccine, *Haemophilus influenzae* (HiB) vaccine, etc. Aluminum adjuvant can only activate Th2 response (humoral immunity based on antibody production), but not Th1 response (cellular immunity based on $CD8^+$ T cells) (10). AS04 is an adjuvant containing MPL and aluminum salts and is used in HPV vaccines and HBV vaccines. The adjuvant can activate NF-kB, produce pro-inflammatory factors, and has the ability to activate Th1 response that the aluminum adjuvant does not originally possess. MF59 is a water-in-oil adjuvant made with squalene as the oil phase. It contains degradable squalene, Tween 80 and Span 85, and is used in influenza vaccines. The mechanism is still unclear. Its half-life in the body is 42 hours, and it can activate both Th1 response and Th2 response at the same time. AS03 is an oil-in-water adjuvant containing alpha tocopherol, squalene, and Tween 80, which is used in influenza vaccines, but the H1N1 influenza virus vaccine Pandemrix™ containing AS03 may cause narcolepsy (11). AS03 can induce the production of pro-inflammatory factors by activating the NF-kB pathway, recruit immune cells, and induce antibody production.

At present, there are many adjuvants that has not been approved in clinical application but can be used in the laboratory, many of which have good effects, but their side effects limit their clinical application. For example, the mineral oil in Freund's adjuvant has poor metabolism, and nodules will form at the injection site. There are also cytokine-type adjuvants, such as interleukin-2 and interferon. Their disadvantage is that they are expensive.

There are currently reports proving that ligands that activate the cGAS-STING pathway can be used as adjuvants, such as DMXAA (12), c-di-GMP (13), cGAMP (14) and chitosan (15).

CN107412260A discloses that divalent manganese is a cGAS-STING pathway activator, which has the effect of enhancing immunity, for example, it can be used as an immunoadjuvant. However, in further research, the inventor unexpectedly found that divalent manganese itself still has some defects, and an improved solution is needed to eliminate at least one of the defects.

SUMMARY

The inventors further studied the immune enhancement effect of divalent manganese and found that although the divalent manganese solution can produce immune enhancement effect in the body, this immune enhancement effect is not high enough. More importantly, during the research process, it was also found that when the concentration of the divalent manganese solution is increased to improve the immune enhancement effect, it is easy to produce manganese precipitation, which makes it impossible to obtain a uniform and stable high-concentration divalent manganese solution, thus the repeatability cannot be effectively guaranteed. This manganese precipitation gradually agglomerates and grows with increasing storage time.

In the case that the desired high-concentration divalent manganese solution is not practicable, the inventors had to use divalent manganese precipitation to continue the research for testing its immune enhancement effect. Due to the negligence of the experimental operation, the inventor inadvertently used divalent manganese precipitates that were left for different periods of time. The inventors unexpectedly found that the divalent manganese precipitates with different storage time has different immune enhancement effects, and the immune enhancement effect of the new precipitates is significantly better than that of the manganese precipitates with a longer storage time. The inventors further compared the divalent manganese solution with the divalent manganese precipitates stored for different time, and unexpectedly found that the immune enhancement effect of the newly precipitated manganese salt was even significantly better than that of the divalent manganese solution.

In the process of testing different divalent manganese systems, the inventors also unexpectedly found that divalent manganese compounds can form colloidal solutions. What is even more surprising is that manganese colloid shows an immune enhancement effect comparable to or even stronger than that of the newly precipitated manganese.

The inventors completed the present invention on the above findings and provided the following technical solutions.

In one aspect, the present disclosure provides a composition for enhancing immunity, which comprises newly precipitated manganese, manganese colloid and/or a source capable of forming newly precipitated manganese and/or manganese colloid.

In one embodiment, the newly precipitated manganese and/or manganese colloid are selected from manganese phosphate, manganese carbonate, manganese hydroxide and a mixture thereof.

Preferably, the conversion time of the newly precipitated manganese from a non-precipitated form to a precipitated form is not more than 1 day, or not more than 24, 22, 20, 18, 16, 15, 14, 12, 10, 9, 8, 7, 6, 5, 4, 3, 2 or 1 hour, or not more than 60, 50, 45, 40, 35, 30, 25, 20, 15, 10, 9, 8, 7, 6, 5, 4, 3, 2 or 1 minute.

In another aspect, the present disclosure provides a vaccine composition comprising
A) a vaccine immunogen, and
B) newly precipitated manganese, manganese colloid and/or a source capable of forming newly precipitated manganese and or manganese colloid.

Optionally, components A and B can be in the same and/or separate containers.

Preferably, the vaccine immunogen is derived from a virus, a bacterium and/or a parasite, For example, the virus is selected from the group consisting of DNA virus and RNA virus, preferably the virus is selected from the group consisting of Herpesviridae, Rhabdoviridae, Filoviridae, Orthomyxoviridae, Paramyxoviridae, Coronaviridae, Picornaviridae, Hepadnaviridae, Flaviviridae, Papillomaviridae, Poxviridae, and Retroviridae, more preferably the virus is selected from the group consisting of herpes simplex virus, vesicular stomatitis virus, vaccinia virus, HIV and HBV.

For example, the bacterium is selected from the group consisting of Gram-negative bacteria and Gram-positive bacteria, preferably the bacterium is selected from the group consisting of *Streptococcus pneumoniae, Haemophilus influenzae, Salmonella, Meningococcus, Staphylococcus epidermidis, Staphylococcus aureus, Escherichia coli, Klebsiella pneumoniae, Klebsiella oxytoca, Enterobacter cloacae, Citrobacter freundii, Pseudomonas aeruginosa* and *Acinetobacter baumanni.*

Specifically, for example, the vaccine immunogen is derived from influenza virus, hepatitis virus (such as hepatitis A virus, hepatitis B virus), polio virus, rabies virus, HPV virus, encephalitis virus (such as Encephalitis B virus), mumps virus, rubella virus, *Clostridium tetani, Bordetella pertussis,* Diphtheria bacillus, *Mycobacterium leprae, Mycobacterium tuberculosis, Neisseria meningitidis, Diplococcus pneumonlae* and a combination thereof.

In another aspect, the present disclosure provides a method of manufacturing a composition for enhancing immunity, which comprises
1) providing a source capable of forming newly precipitated manganese and/or manganese colloid; and
2) optionally converting the source capable of forming newly precipitated manganese and/or manganese colloid into newly precipitated manganese and/or manganese colloid.

Preferably, the newly precipitated manganese and/or manganese colloid are selected from the group consisting of manganese phosphate, manganese carbonate, manganese hydroxide and a mixture thereof.

Preferably, the time for converting the non-precipitated form to the precipitated form to form the newly precipitated manganese is not more than 1 day, or not more than 24, 22, 20, 18, 16, 15, 14, 12, 10, 9, 8, 7, 6, 5, 4, 3, 2 or 1 hour, or not more than 60, 50, 45, 40, 35, 30, 25, 20, 15, 10, 9, 8, 7, 6, 5, 4, 3, 2 or 1 minute.

In another aspect, the present disclosure provides a method of manufacturing a vaccine composition, which comprises
1) providing a vaccine immunogen; and
2) providing a source of newly precipitated manganese, manganese colloid and/or a source capable of forming newly precipitated manganese and/or manganese colloid.

Preferably, the vaccine immunogen is derived from a virus, a bacterium and/or a parasite, as described above, and will not be repeated here.

In one aspect, the present disclosure provides use of newly precipitated manganese, manganese colloid and/or a source of capable of forming newly precipitated manganese and/or manganese colloid in the manufacture of a composition for enhancing immunity or a vaccine composition for improving innate immunity and/or adaptive immunity. In some embodiments, the newly precipitated manganese, manganese colloid and/or the source capable of forming newly precipitated manganese and or manganese colloid improve innate immunity and/or adaptive immunity by increasing the expression of type I interferon. In some other embodiments, the newly precipitated manganese, manganese colloid and/or the source capable of forming newly precipitated manganese and/or manganese colloid improve innate immunity and/or adaptive immunity by inducing cleavage of inflammatory factors to produce an active form of the inflammatory factors. In still some other embodiments, the newly precipitated manganese, manganese colloid and/or a source capable of forming newly precipitated manganese and or manganese colloid improve innate immunity and/or adaptive immunity by promoting antibody production.

In one aspect, the present disclosure provides a method for enhancing immunity, which comprises administering the composition for enhancing immunity to a subject in need thereof.

Specifically, the immune enhancement is, for example, A) to improve innate immunity and/or adaptive immunity, B) to increase expression of type I interferon, C) to induce production of inflammatory factors in active form, D) to promote production of antibodies, E) to promote proliferation of T cells, and/or F) to promote maturation of dendritic cells.

Preferably, the administration is selected from the group consisting of intramuscular injection, intradermal injection, subcutaneous injection, intravenous injection, mucosal administration, and a combination thereof.

In particular, the enhancing immunity is used to prevent and/or treat diseases, such as bacterial infections, fungal infections, viral infections, parasitic infections, tumors, or autoimmune diseases.

Wherein the virus is selected from the group consisting of DNA virus and RNA virus, preferably the virus is selected from the group consisting of Herpesviridae, Rhabdoviridae, Filoviridae, Orthomyxoviridae, Paramyxoviridae, Coronaviridae, Picornaviridae, Hepadnaviridae, Flaviviridae, Papillomaviridae, Poxviridae, and Retroviridae, specifically the virus is selected from the group consisting of herpes simplex virus, vesicular stomatitis virus, vaccinia virus, HIV, influenza virus, hepatitis virus (such as hepatitis A virus, hepatitis B virus), polio virus, rabies virus, HPV virus, encephalitis virus (such as Encephalitis B virus), mumps virus, rubella virus and a combination thereof.

Wherein the bacterium is selected from Gram-negative bacteria and Gram-positive bacteria, preferably the bacterium is selected from the group consisting of *Streptococcus pneumoniae, Haemophilus influenzae, Salmonella, Meningococcus, Staphylococcus epidermidis, Staphylococcus aureus, Escherichia coli, Klebsiella pneumoniae, Klebsiella oxytoca, Enterobacter cloacae, Citrobacter freundii, Pseudomonas aeruginosa, Acinetobacter baumanni*, tetanus *bacillus*, pertussis *bacillus*, diphtheria *bacillus*, leprosy *bacillus*, tuberculosis *bacillus*, meningococcus, pneumococcus and a combination thereof.

Wherein the parasite is an intracellular parasite, preferably selected from the group consisting of *Plasmodium, Toxoplasma, Trypanosoma, Schistosoma, Filaria,* and *Leishmania*.

Wherein the autoimmune disease is selected from type I diabetes, psoriasis, rheumatoid arthritis, systemic lupus erythematosus and multiple sclerosis.

Wherein the tumor is selected from the group consisting of ovarian cancer, lung cancer, gastric cancer, breast cancer, liver cancer, pancreatic cancer, skin cancer, malignant melanoma, head and neck cancer, sarcoma, bile duct cancer, bladder cancer, kidney cancer, colon cancer, placental choriocarcinoma, cervical cancer, testicular cancer, uterine cancer and leukemia.

In some embodiments, the composition for enhancing immunity is administered to a subject in need thereof together with an additional prophylactic therapeutic agent.

In another aspect, the present disclosure provides an immunization method, which comprises:

administering the vaccine composition of the present disclosure to a subject in need thereof, wherein components A and B can be administered at the same time point or at different time points when they are in different containers; and/or administering the composition for enhancing immunity of the present disclosure and an optional vaccine immunogen to a subject in need thereof.

Preferably, the administration is selected from intramuscular injection, intradermal injection, subcutaneous injection, intravenous injection, mucosal administration and a combination thereof.

In particular, the immunization is used to prevent diseases such as bacterial infections, fungal infections, viral infections, parasitic infections, tumors, and autoimmune diseases. The diseases are the same as those mentioned above, so they are not repeated here.

In some embodiments, the composition for enhancing immunity is administered to a subject in need thereof together with another prophylactic/therapeutic agent.

In yet another aspect, the present disclosure provides use of newly precipitated manganese, manganese colloid and/or a source capable of forming newly precipitated manganese and/or manganese colloid in the manufacture of a medicament for enhancing type I interferon function.

In yet another aspect, the present disclosure provides use of newly precipitated manganese, manganese colloid and/or a source capable of forming newly precipitated manganese and/or manganese colloid in the manufacture of a medicament for inducing cleavage of inflammatory factors to produce an active form thereof.

In yet another aspect, the present disclosure provides use of newly precipitated manganese, manganese colloid and/or a source capable of forming newly precipitated manganese and/or manganese colloid in the manufacture of a medicament for stimulating antibody production.

In yet another aspect, the present disclosure provides use of newly precipitated manganese, manganese colloid and/or a source capable of forming newly precipitated manganese and/or manganese colloid as an immunoadjuvant. In some embodiments, the immunoadjuvant activates T cell activation and/or antibody production. Preferably, the immunoadjuvant is used in a vaccine composition for the treatment of diseases selected from bacterial infections, viral infections, parasites, autoimmune diseases and cancer.

In yet another aspect, the present disclosure provides a kit for immunization, comprising: a first container containing one or more antigens therein; and a second container containing newly precipitated manganese, manganese colloid and/or a source capable of forming newly precipitated manganese and/or manganese colloid. Preferably, the first container and/or the second container further comprise a pharmaceutically acceptable carrier. In particular, the kit is used for one or more purposes of the present disclosure. In some embodiments, the antigen and the newly precipitated manganese, manganese colloid, and/or the source capable of forming newly precipitated manganese and/or manganese colloid are in the same container.

In some embodiments, the antigen used in the present disclosure is selected from the group consisting of viral or bacterial or parasite antigens, for example, hepatitis viruses A, B, C, D and E-3, HIV, herpes virus types 1, 2, 6 and 7, cytomegalovirus, varicella-zoster virus, papilloma virus, Epstein-Barr virus, influenza virus, parainfluenza virus, adenovirus, Bunya virus (Hantavirus), Coxasackie virus, picornavirus, rotavirus, respiratory syncytial virus, pox virus, rhinovirus, rubella virus, papilloma virus, mumps virus and measles virus, mycobacterium that causes tuberculosis and leprosy, pneumococcus, aerobic Gram-negative bacilli, mycoplasma, staphylococcal infections, streptococcal infections, salmonella and chlamydia, *Helicobacter pylori*, malaria, leishmaniasis, trypanosomiasis, toxoplasmosis, schistosomiasis, and filariasis.

In some embodiments, the newly precipitated manganese, manganese colloid, and/or the source capable of forming newly precipitated manganese and/or manganese colloid, and/or antigen in the present disclosure are in an effective amount.

In yet another aspect, the present disclosure provides a method for increasing expression of type I interferon in a subject, which comprises administering to the subject newly precipitated manganese, manganese colloid and/or a source capable of forming newly precipitated manganese and/or manganese colloid. In addition, the present disclosure also provides a method for enhancing the activity of type I interferon in cells in vitro, which comprises applying newly precipitated manganese, manganese colloid and/or a source capable of forming newly precipitated manganese and/or manganese colloid to the cells. Preferably, the method is for non-therapeutic purposes.

In yet another aspect, the present disclosure provides a method for inducing cleavage of inflammatory factors to produce an active form thereof in a subject, which comprises administering to the subject newly precipitated manganese, manganese colloid and/or a source capable of forming newly precipitated manganese and/or manganese colloid. In addition, the present disclosure also provides a method for inducing cleavage of inflammatory factors in cells to produce active forms in vitro, which comprises applying to said cells newly precipitated manganese, manganese colloid and/ or a source capable of forming newly precipitated manganese and/or manganese colloid. Preferably, the method is for non-therapeutic purposes.

In yet another aspect, the present disclosure provides a method for stimulating antibody production in a subject, which comprises administering to the subject newly precipitated manganese, manganese colloid and/or a source capable of forming newly precipitated manganese and/or manganese colloid. In addition, the present disclosure also provides a method for stimulating cells to produce antibodies in vitro, which comprises applying newly precipitated manganese, manganese colloid and/or a source capable of forming newly precipitated manganese and/or manganese colloid to the cells. Preferably, the method described is for non-therapeutic purposes.

DESCRIPTION OF THE DRAWINGS

Hereinafter, the aforementioned aspects and other aspects of the present disclosure will be clearly explained through the detailed description of the present disclosure and the accompanying drawings. To illustrate the present disclosure, the embodiments in the drawings are currently preferred, however, it is understood that the present disclosure is not limited to the specific embodiments disclosed.

FIG. 1A shows the different states of divalent manganese in solution; FIG. 1B shows the transmission electron microscope image of manganese colloid ($Mn_2OHPO_4$); FIG. 1C shows the level of OVA antibody IgG1 after immunization; FIG. 1D shows the comparison of retention time after intramuscular injection of $MnCl_2$ solution and manganese colloid ($Mn_2OHPO_4$).

FIG. 2A shows different states formed by $MnCl_2$ solution and different concentrations of carbonate ion, bicarbonate ion, phosphate ion, monohydrogen phosphate ion, and hydroxide ion; FIG. 2B shows the ability of manganese ions in different states to activate type I interferon, to induce the production of inflammatory factor IL-10, and to act as an adjuvant mixed with OVA protein to produce antibodies; FIG. 2C shows the Tyndall effect of the products formed by manganese ions and different anions, using a laser pointer.

FIGS. 6A-B show the expression levels of type I interferon, downstream inducible factors ISG54 and viperin after $MnCl_2$ treatment of mouse peritoneal macrophages, with aluminum adjuvant as a control. FIGS. 6C-D show that $MnCl_2$ activates inflammasome activation, with aluminum adjuvant as a control. FIGS. 6E-F show that the activation of inflammasomes activated by $MnCl_2$ is dependent on NLRP3 and ASC.

FIG. 9A shows that manganese colloid ($MnOHPO_4$) induces the maturation of antigen-presenting cells BMDC. FIG. 9B shows that manganese colloid ($MnOHPO_4$) plus antigen OVA stimulates the proliferation of $CD4^+$ T cells. FIG. 9C shows that manganese colloid ($MnOHPO_4$) is used as an adjuvant to stimulate $CD8^+$ T cell activation after immunizing mice.

FIG. 10A shows the experimental flow. FIG. 10B shows that the inactivated VSV virus was diluted to doses of $10^{-1}$, $10^{-2}$, $10^{-3}$, $10^{-4}$, $10^{-5}$, $10^{-6}$ to immunize mice, and the survival rate of the mice was observed after 14 days. FIG. 10C shows the death curve of mice was observed for 14 days after immunizing mice with VSV inactivated virus diluted to a dose of $10^{-3}$. FIG. 10D shows the virus titers in the brains of mice on Day 4 of infection with the VSV virus. FIGS. 10E-G shows that adding manganese colloid to the inactivated HSV-1 virus has the similar protection effect.

FIGS. 11A-B shows the survival rate and body weight change of mice infected with influenza virus 7 days after intranasal instillation with the inactivated influenza virus diluted to doses of 1, $10^{-1}$, $10^{-2}$, and $10^{-3}$. FIGS. 11C-D shows the survival rate and body weight change of mice infected with influenza virus after immunizing mice twice with intranasal drops.

FIG. 12A shows the anti-HA IgG1 antibody content in the mouse serum 14, 21, and 28 days after intramuscular injection of mice. FIG. 12B shows the anti-HA IgA antibody content in the serum of mice 14 days, 21 days, and 28 days after the nasal drip immunization of the mice. FIG. 12C shows the body weight changes of mice after infection with influenza virus. FIG. 12D shows the pathological changes of mouse lung tissue on Day 5 of infection.

FIG. 13A shows the weight change of WSN virus-infected mice after immunization; FIG. 13B shows the weight change of H3N2 virus-infected mice after immunization.

FIG. 14A are images at different times, showing the size of the subcutaneous tumors. FIG. 14B shows the change in tumor volume after tumor inoculation.

FIG. 14C shows the survival curve of mice after tumor inoculation. FIG. 14D shows that the tumor metastasized lung tissue which was photographed 21 days after different immunization methods. FIG. 14E shows the statistics of the number of tumor cells in FIG. 14D.

FIG. 15A shows pictures of tumors 14 days after different treatments. FIG. 15B shows the growth curve of mouse subcutaneous B16-F10 tumor. FIG. 15C shows the tumor weight of the mice in the corresponding group on Day 14 in FIG. 15B.

FIG. 16A shows pictures of tumors after different treatments. FIG. 16B shows the growth curve of the tumor. FIG. 16C shows the tumor weight of the mice in the corresponding group in Figure B. FIGS. 16D-E shows the number of $CD8^+$ T cells infiltrated in the tumor analyzed by flow cytometry.

FIG. 17A shows pictures of tumors after different treatments. FIG. 17B shows the growth curve of the tumor. FIG. 17C shows the tumor weight of the corresponding group in FIG. 17B. FIG. 17D shows a tissue section of the tumor in the corresponding group in FIG. 17A, with immunofluorescence staining of DAPI and $CD8^+$ T cells.

DETAILED DESCRIPTION

Definitions

Figure 1:
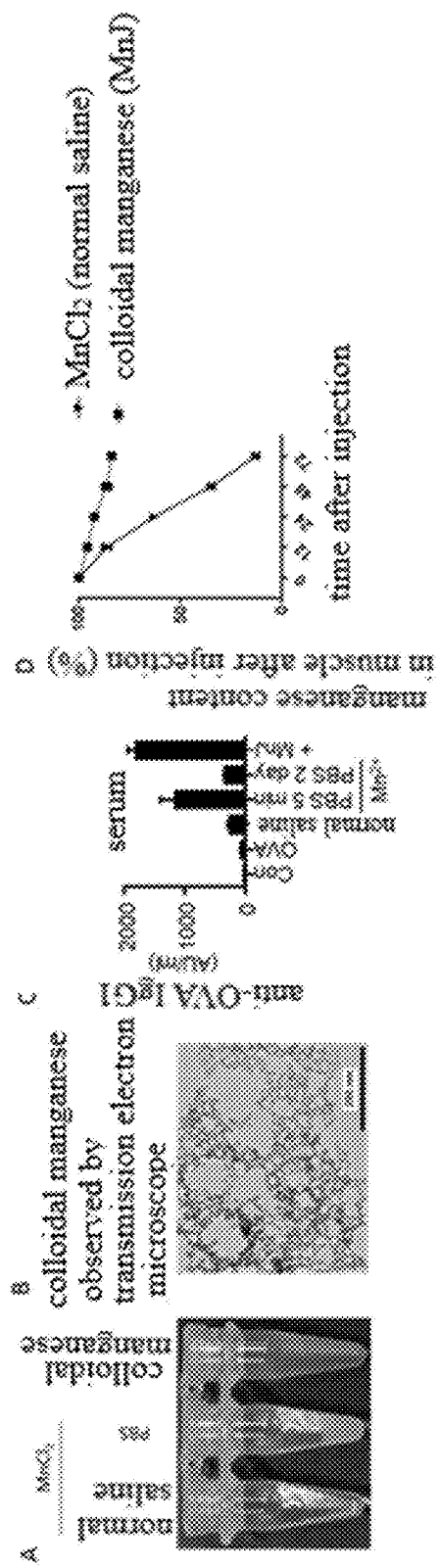
FIG. 1 illustrates that newly precipitated manganese and manganese colloid ($Mn_2OHPO_4$) are good adjuvants.

The term "innate immunity" as used herein refers to the natural immune defense function formed during germline development and evolution, that is, the non-specific defense function already possessed after birth, also known as non-specific immunity. Innate immunity involves a variety of cells and molecules, such as macrophages, natural killer cells, complement, cytokines (IL, CSF, IFN, TNF, TGF-β), chemokines (including CC chemokines, such as CCL1, CCL2), CCL3, CCL4, CCL5, CCL6, CCL7, CCL8, CCL9, CCL10, CCL11, CCL12, etc. CXC chemokines, such as CXCL1, CXCL2, CXCL3, CXCL4, CXCL5, CXCL6, CXCL7, CXCL8, CXCL9, etc., C chemokine, CX3C chemokine), lysozyme and so on.

The term "adaptive immunity" as used herein, also known as acquired immunity or specific immunity, refers to the specific immunity of the body against the antigen formed after the stimulation of the antigen molecule, which involves cellular immunity and humoral immunity.

The term "adjuvant" or "immunoadjuvant" as used herein refers to an agent that does not constitute a specific antigen, but enhances the strength and duration of the immune response to the co-administered antigen.

The term "divalent manganese" or "divalent manganese compound" as used herein can be hydrochloride, carbonate, hydrobromide, sulfate, nitrate, phosphate, tartrate, fumarate, maleate, lactate, benzenesulfonate, pantothenate, ascorbate, hydroxide, etc., or a combination thereof. Preferably, the divalent manganese compound is pharmaceutically acceptable.

The term "colloidal manganese" or "manganese colloid" as used herein refers to a colloid formed by divalent manganese and anion, which is in a state of colloid (also known as colloidal solution). The term "colloid" is understood by those of ordinary skill in the art. For example, the particle size of colloidal particles is generally about 1 to 100 nm, especially 1, 2, 3, 4, 5, 6, 7, 8, 9, 10, 15, 20, 25, 30, 35, 40, 45, 50, 60, 70, 80, 90, 100 nm, or a value between any two of the above values, such as 1 to 20, 5 to 20 nm, 10 nm. Typically, colloidal solutions exhibit the Tyndall effect when exposed to light. Considering that the particle size range of colloidal particles is on the order of nanometers, "manganese colloid" herein can also be referred to as "nano manganese" according to its particle size range.

The term "newly precipitated manganese" as used herein refers to a divalent manganese compound which exists in a state short period after the conversion from a non-precipitated form (such as a solution form) to a precipitated form. The short period generally is not more than 1 day, and typically not more than 24, 22, 20, 18, 16, 15, 14, 12, 10, 9, 8, 7, 6, 5, 4, 3, 2 or 1 hour, such as not more than 60, 50, 45, 40, 35, 30, 25, 20, 15, 10, 9, 8, 7, 6, 5, 4, 3, 2 or 1 minute.

Terms such as "comprising", "including", "containing" and "comprise" as used herein are not intended to be limiting. In addition, unless otherwise stated, "or" means "and/or".

As used herein, "derived from a virus, a bacterium and/or a parasite" means to include inactivated viruses, bacteria and/or parasites, or proteins and/or nucleic acids extracted from the above pathogenic substances (also includes the above-mentioned substances after cutting, engineering, etc.), or purified recombinant protein substances, or chemically synthesized peptide fragment substances.

In addition, it should be noted that, as used in this specification, the singular form includes the plural form of the referent, unless it is clearly and clearly limited to one referent. And if a specific value is mentioned, at least that value will be included, unless it clearly indicates in this disclosure that it refers otherwise.

When a numerical value represents an approximate value, it should be understood that the specific numerical value forms another embodiment. As used, "about X" (where X is a number) means±10% (inclusive) of the listed value. If present, all ranges are inclusive and combinable.

The term "pharmaceutically acceptable carrier" as used herein can be selected from the group consisting of water, buffered aqueous solutions, isotonic salt solutions such as PBS (phosphate buffered saline), glucose, mannitol, dextrose, lactose, starch, magnesium stearate, cellulose, magnesium carbonate, 0.3% glycerin, hyaluronic acid, ethanol or polyalkylene glycols such as polypropylene glycol, triglycerides, etc. The type of pharmaceutically acceptable carrier used depends inter alia on whether the composition according to the invention is formulated for oral, nasal, intradermal, subcutaneous, intramuscular or intravenous administration. The composition according to the present disclosure may contain lubricants, preservatives, stabilizers, wetting agents, emulsifiers, salts that affect osmotic pressure, buffers, coloring substances, flavoring substances and/or aromatic substances and the like as additives.

The pharmaceutical composition according to the present disclosure can be administered by any suitable route, for example, it can be administered orally, nasally, intracutaneously, subcutaneously, intramuscularly or intravenously.

The term "administration" as used herein means to provide a substance to a subject in a pharmacologically usable manner.

As used herein, "pharmaceutical effective amount" and "effective amount" refer to a dose sufficient to show its benefit to the subject to which it is administered. The actual amount administered, as well as the rate and time course of administration, will depend on the condition and severity of the person being treated. The prescription of treatment (such as the decision on dosage, etc.) is ultimately the responsibility of the general practitioner and other doctors and rely on them to make decisions, usually taking into account the disease to be treated, the individual patient's condition, the location of delivery, the method of application, and other factors already known to the doctor.

The term "subject" as used herein means animals, including warm-blooded mammals such as humans and primates; birds; domesticated domestic or farm animals such as cats, dogs, sheep, goats, cattle, horses and pigs; laboratory animals such as mice, rats and guinea pigs; fish; reptiles; zoo animals and wild animals, etc.

Unless otherwise defined, all scientific and technological terms used herein have the same meaning as understood by those of ordinary skill in the art.

Unless otherwise specified, any component, element, attribute or step disclosed in an embodiment of the method and product can be applied to any other method and product disclosed herein.

Each patent, patent application, or cited publication of the present disclosure or description in this document is incorporated herein by reference in its entirety.

The present disclosure is further defined in the following examples. It should be understood that these examples are only described by way of example, and are not intended to limit the scope of the present disclosure. From the above discussion and these examples, those skilled in the art can ascertain the essential features of the present disclosure, and without departing from its essence and scope, can make various changes and modifications to the present disclosure to adapt it to various uses and conditions.

EXAMPLES

Materials and Methods

Antibodies and Regents

The sources of the antibodies are as follows: anti-GAPDH antibody (sc-25778) was purchased from Santa Cruz. Anti-viperin antibody, anti-ISG54 antibody, anti-Casp1/p20 antibody, anti-IL1β/p17 antibody and anti-ASC antibody were all prepared and used according to known methods (16). In short, the cDNA of the antigen fragment was inserted into the pET-21b vector (Novagen) and expressed in *E. coli* BL21 (DE3), and the recombinant protein was purified by Ni-NTA affinity column and then injected into mice or rabbits, thereby the antiserum that can recognize the corresponding antigen was obtained.

All chemicals were purchased from Sigma-Aldrich (St. Louis, MO), unless otherwise stated. Aluminum adjuvant (Imject Alum, Thermo, 77161), mouse IL-1beta ELISA Kit (MULTI SCIENCES, EK201B2/2), mouse IL-18 ELISA Kit (MULTI SCIENCES, EK2181), lipopolysaccharide (Sigma, L4130), ovalbumin (InvivoGen, #vac-pova) were all commercial products.

Cell

L929-ISRE (obtained by stably transfecting pGL3 ISRE-Luciferase plasmid into L929 cells, ATCC® CCL-1), BHK21 (ATCC® CCL-10), B16-OVA (ATCC® CRL)-6322) and B16F10 (ATCC® CRL-6475) cells were cultured in DMEM (Gibco) medium supplemented with 10% FBS (Gibco), 5 μg/ml penicillin and 10 μg/ml streptomycin. Bone marrow derived macrophages (BMDCs) were induced in RPMI-1640 (Gibco) medium containing 10 ng/mL GM-CSF, 10 ng/mL IL-4, and 10% FBS (Gibco). The medium was changed in half on the $3^{rd}$ day, and the experiment was carried out on Day 7. Peritoneal macrophages were harvested from mice 5 days after induction with mercaptoglycolate (BD, Sparks, MD) and cultured in DMEM medium supplemented with 5% FBS.

Mouse

Tmem173$^{-/-}$ mice were established by CRISPR-cas9 method by injecting Cas9 mRNA (100 ng/μl) and gRNA (50 ng/μl) into cytoplasm of zygotes of C57BL/6J mouse. Cas9 mRNA and single guide RNA (gRNA) were transcribed in vitro by mMESSAGE mMACHINE T7 Ultra (Ambion, am1345). Nlrp3$^{-/-}$, Nlrc4$^{-/-}$, Pycard$^{-/-}$ and Aim2$^{-/-}$ knock-out mice were provided by Vishva Dixit (Genentech Inc, USA). Tmem173$^{-/-}$ Pycare double knock-out mice were identified by mating Tmem173$^{-/-}$ mice with Pycard$^{-/-}$.

All mice were housed in the Laboratory Animal Center of Peking University under aseptic conditions in accordance with the National Institute of Health Guide for Care and Use of Laboratory Animals (NIH).

Type I IFN (IFN-I) Bioassay

The concentration of type I IFN was determined according to the published method (17). In short, IFN-stimulated response element (ISRE) was cloned into pGL3-Basic vector (Promega) to construct an IFN-sensitive luciferase vector, which was then stably transfected into L929 cells. The L929-ISRE cells were seeded into a 96-well plate and incubated with the cell culture supernatant. Recombinant human and mouse IFN-β (R&D Systems) were used as standards. After 4 hours, L929-ISRE cells were lysed and assayed by Luciferase Reporter Assay System (Promega).

Viral Infection

Herpes simplex virus 1 (HSV-1, from Hongbing Shu, Wuhan University, ATCC® VR-1544) and vesicular stomatitis virus (VSV, Indiana strain, ATCC® VR-1238) were kindly donated by the above-mentioned colleague. H1N1 influenza virus PR8 strain (from Yonghui Zhang, Tsinghua University, ATCC® VR-95). H1N1 influenza virus WSN strain, A/WSN/33(H1N1) (from Wenjun Liu, Institute of Microbiology, CAS). H3N2 influenza virus strain, H3N2 subtype A/Jiangxi/2005 (from Min Fang, Institute of Microbiology, CAS). BHK21 cells were used to determine the titers of HSV-1 and VSV viruses. MDCK cells were used to determine influenza virus titer.

Virus amplification and purification: HSV-1 and VSV viruses were amplified in vero cells. PR8, WSN, and H3N2 influenza viruses were amplified in chicken embryos. The amplified virus was purified with PEG8000, and the purified virus was inactivated with 0.2% formaldehyde at 37 degrees Celsius for 24 hours. The plaque assay was used to measure whether the virus was completely inactivated, and then the inactivated virus was used to immunize mice.

Mouse survival experiment: Infect 8-12 weeks old mice intravenously with HSV-1 ($1.4 \times 10^7$ pfu/mouse) and VSV ($8 \times 10^8$ pfu/mouse); or infect 8-12 weeks old mice intranasally with PR8 ($1 \times 10^5$ pfu/mouse), WSN ($1 \times 10^6$ pfu/mouse), and H3N2 ($1 \times 10^6$ pfu/mouse).

Plaque assay: BHK21 cells were incubated with homogenates (a series of dilutions in serum-free DMEM) from infected mouse organs for 2 hours. Then, the medium was replaced with serum-free DMEM containing 0.5% methylcellulose. After 60 hours, the cells were fixed with 0.5% (vol/vol) glutaraldehyde and stained with 1% (wt/vol) crystal violet (dissolved in 70% ethanol). The plaques were counted to calculate the virus titer in plaque forming units.

Protein Expression and Purification

Influenza virus HA1 protein purification plasmid was provided by Zhang Yonghui Laboratory of Tsinghua University (18). The plasmid expressed the 11-324 amino acids of HA protein (Gene ID: 956529). When the bacterial broth reached an $OD_{600}$ of 0.6, 0.5 mM IPTG was added and incubated at 37° C. for 5 hours. After the bacteria were collected, the inclusion bodies were collected after ultrasound treatment, and the HA1 protein was obtained after denaturation and renaturation. Then the HA1 protein was purified by gel filtration chromatography.

Mice Immunization Using Ovalbumin (OVA) as an Immunogen

The immunization by intramuscular injection using $MnCl_2$ solution as adjuvant was performed by adding 10 μg $MnCl_2$ and 10 μg OVA protein to 100 μL PBS, mixing well and standing for 5 minutes, and then immunizing mice by intramuscular injection. The immunization by intranasal route using $MnCl_2$ solution as adjuvant was performed by adding 5 μg $MnCl_2$ and 10 μg OVA protein to 20 μL PBS, mixing well and standing for 5 minutes and then immunizing mice by intranasal route. The immunization by intramuscular injection using manganese colloid as adjuvant ($Mn_2OHPO_4$ as an example) was performed by adding 10 μg manganese colloid and 10 μg OVA protein to 100 μL of normal saline, mixing well and intramuscularly immunizing mice. The immunization by intranasal route using manganese colloid as adjuvant was performed by adding 5 μg manganese colloid and 10 μg OVA protein to 20 μL of normal saline, mixing well and immunizing mice by intranasal route. The immunization by intramuscular injection using aluminum adjuvant was performed by adding 10 μg/20 μL aluminum adjuvant and 10 μg OVA protein to 80 μL normal saline, emulsifying with an emulsifier and then immunizing mice by intramuscular injection. The immunization by intranasal route using Cholera toxin B (CTB) as adjuvant was performed by adding 5 μg CTB and 10 μg OVA protein to 20 μL normal saline, mixing well and immunizing mice by intranasal route.

Determination of OVA-specific IgG1, IgG2c, total IgG, and IgA antibodies by ELISA: The diluted serum from immunized mice was incubated in ELISA plate coated with 100 μg/ml OVA. After washing, HRP-conjugated mouse IgG1 (eBioscience, #18-4015-82), IgG2c (GeneTex, GTX77297), IgG total (Invitrogen, G21040), IgA (GeneTex, GTX77223) were used to detect the bound corresponding antibodies. Then, the plate was incubated with the substrate TMB (eBioscience), the reaction was terminated by 1 M $H_3PO_4$, and then the absorbance at 450 nm was measured.

Statistical Analysis

T-test was used to analyze data. The Mantel-Cox test was used to compare survival curves.

Example 1. States of Manganese Compounds in Solution and its Effect as Adjuvant

Experiment (a) Precipitates Formed by Reaction Between $MnCl_2$ and PBS, Preparation of Manganese Colloid $Mn_2OHPO_4$ As shown in FIG. 1A, in the experiments, normal saline (0.9% NaCl) was prepared in the laboratory, and PBS (pH 7.4) was purchased from Gibco. There were 3 reaction systems: (1) 100 μl $MnCl_2$ (0.2 M) with 900 μl saline; (2) 100 μl $MnCl_2$ (0.2 M) with 900 μl PBS; (3) 50 μl $Na_3PO_4$ with 850 μl saline, then 100 μl $MnCl_2$ (0.2 M) was added to make manganese colloid. The molecular formula of the manganese colloid was determined by X-ray photoelectron spectroscopy (XPS) to be $Mn_2OHPO_4$ in this experiment. There is no precipitate in normal saline (1), and a white precipitate was generated when reacting with PBS (2) overnight. The product produced by reaction (3) was not a precipitate but a colloid, which showed Tyndall effect when a light beam passed through. The fine structure of the manganese colloid was photographed with a transmission electron microscope, as shown in FIG. 1B, and the size of the particles was about 10 nm in diameter.

Experiment (b) Comparison of the Adjuvant Effect Between Manganese Compound Precipitates in PBS and Manganese Colloid The mice were randomly divided into 6 groups according to their body weight: 1) PBS control group; 2) antigen OVA (10 μg); 3) 2-day reaction group, $MnCl_2$ in normal saline (10 μg $MnCl_2$+OVA); 4) 5-minute reaction group, $MnCl_2$ in PBS (10 μg $MnCl_2$+OVA); 5) 2-day reaction group, $MnCl_2$ in PBS (10 μg $MnCl_2$+OVA); 6) 30-day group, manganese colloid (10 μg $Mn_2OHPO_4$+OVA). The 10 μg here refers to the mass of the element manganese. Each group was used for mice immunization by intramuscular injection according to the experimental design, and the mice were immunized on Day 0, Day 7, and Day 14. On Day 21, blood was taken, serum was separated, and the content of IgG1 antibody against OVA was measured by ELISA. As shown in FIG. 1C, the product from the reaction of $MnCl_2$ and PBS for a short time has an adjuvant effect, but for the product after a long time of reaction, the effect was weakened due to agglomerating into large particles. In the contract, the effect of manganese colloid (abbreviated as MnJ in the figure) $Mn_2OHPO_4$ remained good after being stored for one month. This indicates that manganese colloid is a good and stable adjuvant.

Experiment (c) Comparison of the Retention Time of $MnCl_2$ Solution and Manganese Colloid ($Mn_2OHPO_4$) at the Injection Site The mice were randomly divided into 2 groups according to body weight, namely: intramuscular injection of $MnCl_2$ solution group (20 μg $MnCl_2$ dissolved in 100 μl saline), and intramuscular injection of manganese colloid group (20 μg manganese colloid suspended in 100 μl saline). 20 μg here refers to the mass of the element manganese. At different times after the injection, 0.1 g of the muscle at the injection site was taken, digested with a microwave digestion apparatus, and then the content of the element manganese was determined by ICP-MS (Thermo X SERIES II). As shown in FIG. 1D, manganese colloid can stay at the injection site longer, which can activate the body to produce antibodies more persistently, while manganese in solution was quickly metabolized.

Example 2. Properties and Cellular Effects of the Precipitates Generated by Reaction of Manganese (II) Ion with Other Anions Experiment (a) Reacting Fixed Concentration of Manganese (II) Ion with Different Concentrations of Anions In the normal saline reaction system, 20 mM $MnCl_2$ was reacted with other anions ($Na_2CO_3$, $NaHCO_3$, $Na_3PO_4$, $Na_2HPO_4$, NaOH) at different concentrations (2.5, 5, 10, 20, 30, 40 mM) from sodium salts. As shown in FIG. 2A, divalent free manganese reacts with $CO_3^{2-}$ to produce black $MnCO_3$ precipitate; reacts with $HCO_3^-$ to produce white Mn(HCO$_3$)$_2$ precipitate; reacts with low concentration PO$_4^{3-}$ to produce white precipitate and reacts with high concentration PO$_4^{3-}$ to produce slightly yellow colloidal substance, and these two products were determined to be Mn$_3$(PO$_4$)$_2$ at low concentration and Mn$_2$OHPO$_4$ at high concentration; divalent free manganese reacts with HPO$_4^{2-}$ to produce white MnHPO$_4$ precipitate; and reacts with OH$^-$ to produce yellowish Mn(OH)$_2$ precipitate.

Experiment (b) Comparison of the Ability of Different Manganese (II) Ion Products to Activate Type I Interferon and Promote the Cleavage of Inflammatory Factors to Produce IL-1β, and the Adjuvant Effect As shown in FIG. 2B, in the order from left to right, in Eppendorf tubes, 100 μL 0.2 M MnCl$_2$ was added with the follows respectively,

- 900 μL normal saline overnight (MnCl$_2$),
- 100 μL 0.5 M NaHCO$_3$+800 μL normal saline, and placed overnight (Mn(HCO$_3$)$_2$ was produced),
- 100 μL 0.5 M Na$_2$CO$_3$+800 μL normal saline, and placed overnight (MnCO$_3$ was produced),
- 20 μL 0.5 M Na$_2$CO$_3$+20 μL 0.5 M NaOH+860 μL normal saline, and placed overnight (Mn$_2$OHCO$_3$ was produced),
- 100 μL 0.5 M NaH$_2$PO$_4$+800 μL normal saline, and placed overnight (Mn(H2PO$_4$)$_2$ was produced),
- 100 μL 0.5 M Na$_2$HPO$_4$+800 μL normal saline, and placed overnight (MnHPO$_4$ was produced),
- 26.6 μL 0.5 M Na$_3$PO$_4$+873.4 μL normal saline, and placed overnight (Mn$_3$(PO$_4$)$_2$ was produced),
- 50 μL 0.5 M Na$_3$PO$_4$+850 μL normal saline, and placed overnight (Mn$_2$(OH)PO$_4$ was produced), and
- 100 μL 0.5 M NaOH+800 μL normal saline, and placed overnight (Mn(OH)$_2$ was produced).

Figure 2:
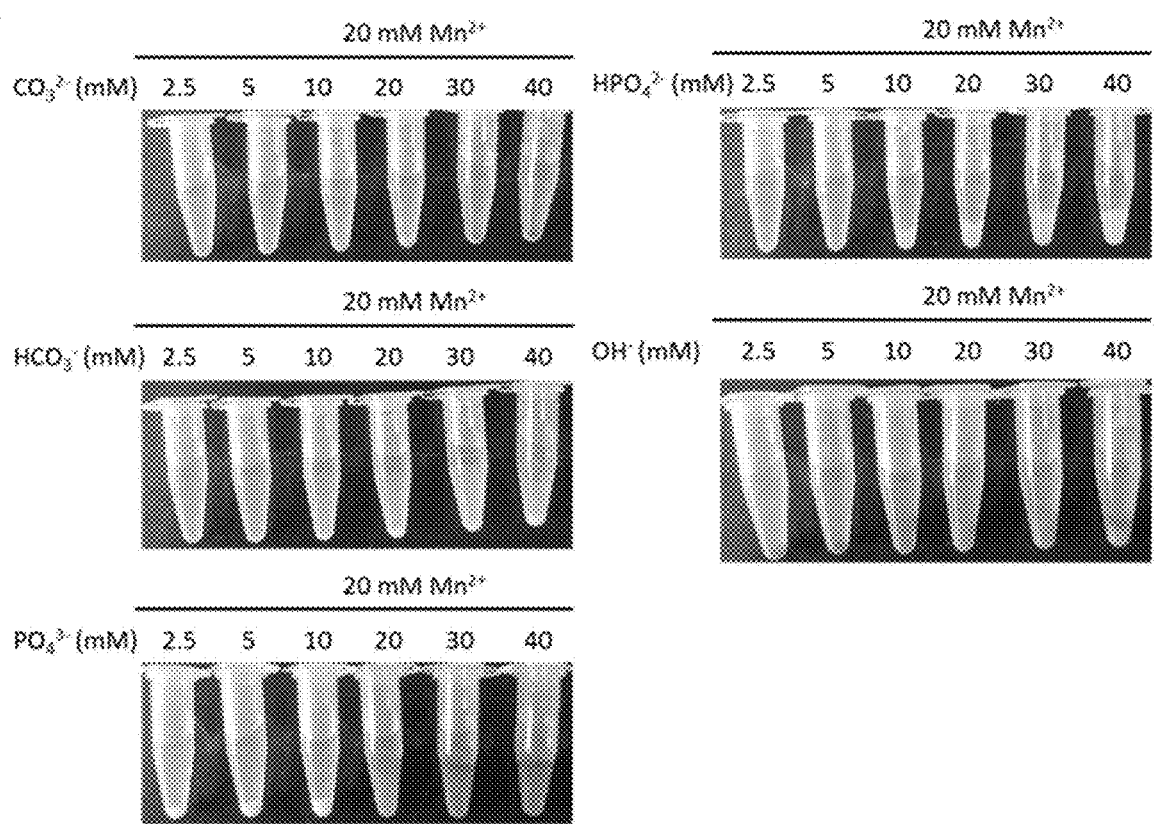
FIG. 2 illustrates the different existing states and properties of $MnCl_2$ solution mixed with other anions in normal saline, the ability of these precipitates or colloids to activate type I interferon or inflammatory factors, and as adjuvant.
Figure 2:
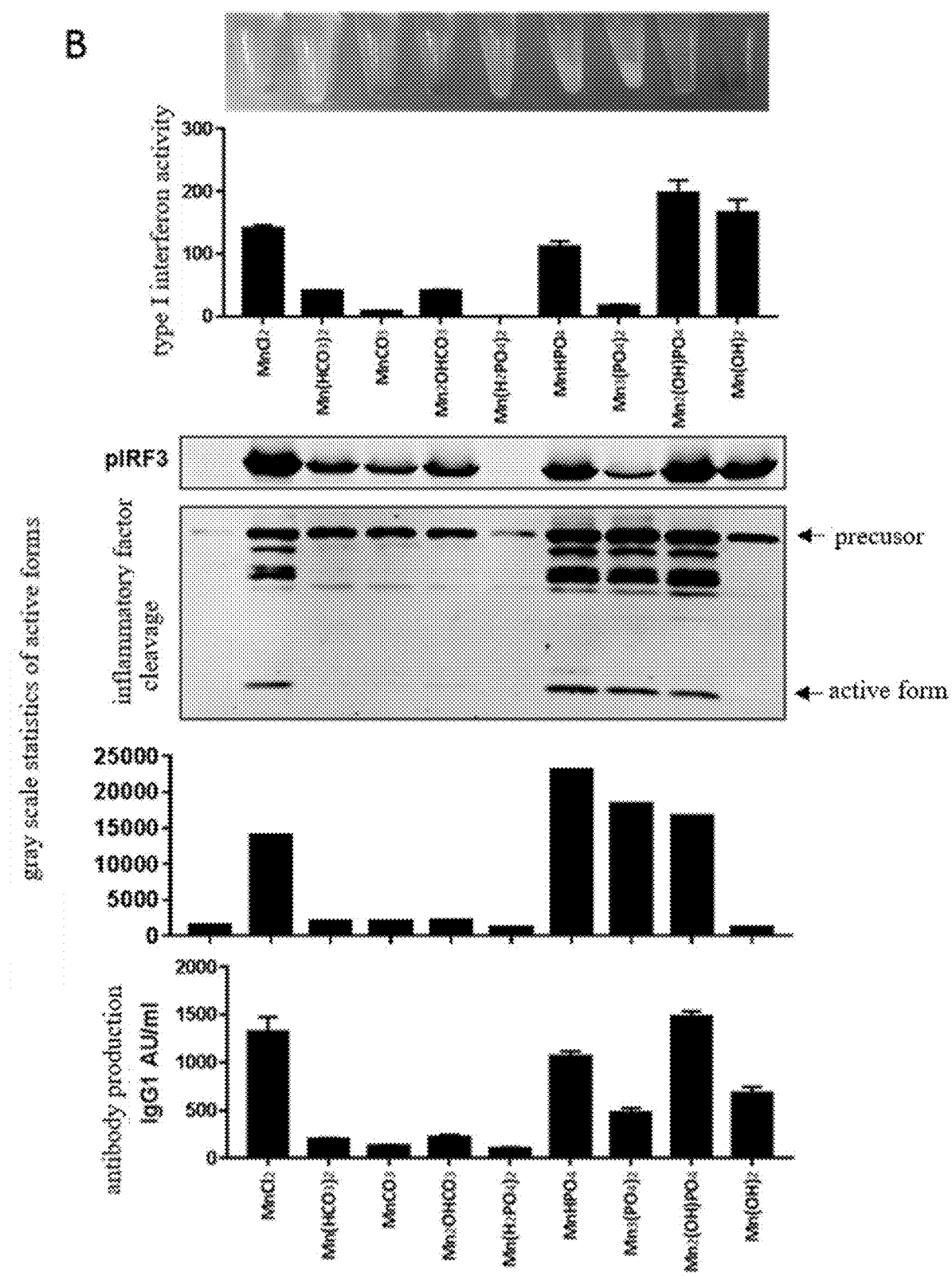
Figure 2:
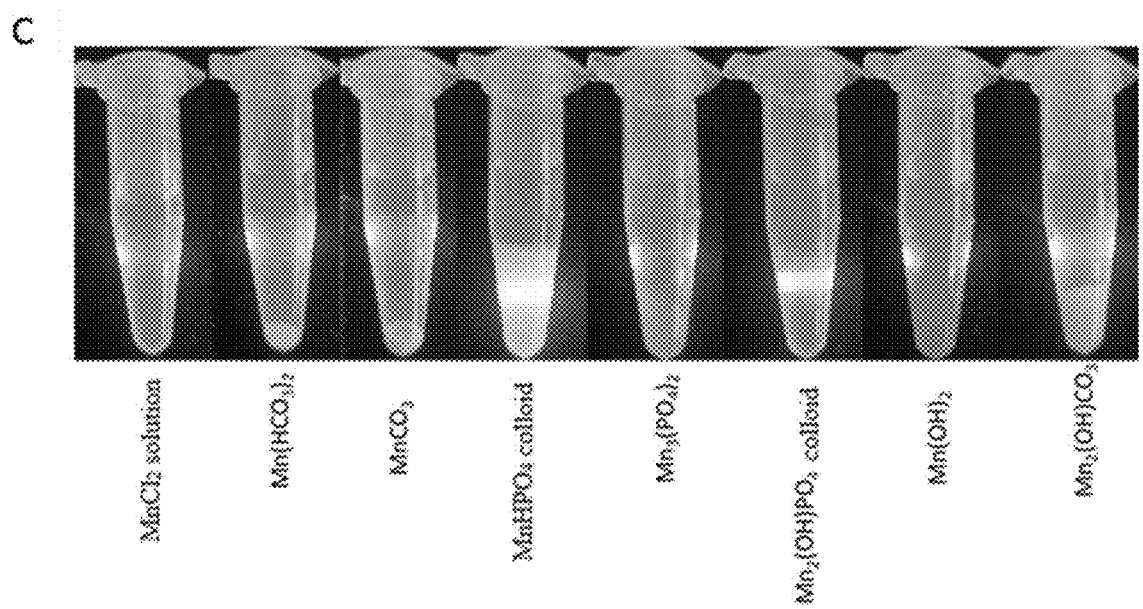

The above reactions produced colloid or solid precipitates as shown in FIG. 2. The precipitates were washed once with normal saline and used for subsequent experiments (For MnCl$_2$, no washing was performed because there was no precipitation in the saline, so the solution was used for the experiment). Equimolar amounts (containing 500 μM of Mn$^{2+}$) of various products were used to stimulate 2×10$^6$ THP1 cells for 18 hours and the level of type I interferon in the supernatant was determined. Among the products, Mn(H2PO$_4$)$_2$ product had little precipitate and the concentration was less than 500 μM since it is easily soluble in water, while other anions can precipitate all Mn'. The results are shown in FIG. 2B. Mn$_2$OHPO$_4$ and MnHPO$_4$ significantly activates the production of type I interferon. As shown in the figure, P-IRF3 is the main transcription factor regulating the expression of type I interferon. Mn$_2$OHPO$_4$ and MnHPO$_4$ also significantly induce the production of IL-1β. But non-colloid Mn(OH)$_2$ can only activate the production of type I interferon, not the production of inflammatory factor IL-1β. Mice were immunized with a mixture of 10 μg of the product (10 μg refers to the mass of manganese element) and 10 μg OVA protein each time, for three times. Each of the products was tested. The mouse serum was taken and the content of the IgG1 antibody against OVA was measured. Mn$_2$OHPO$_4$ and MnHPO$_4$ stimulate the body to produce antibodies significantly better than the precipitated manganese compounds. The leftmost bar in the figure represents the adjuvant effect of the precipitate which is formed by the reaction of MnCl$_2$ with PBS for 5 minutes. Other precipitates formed by overnight reaction also have a partial adjuvant effect. The manganese colloid Mn$_2$OHPO$_4$ which showed the best effect in the experiment was selected for follow-up experiments.

Experiment (c) Comparison of Tyndall Effect of Different Manganese (II) Ion Products As shown in FIG. 2C, the reaction product was resuspended in normal saline and a laser pointer was used as a light source. It can be seen that the Tyndall effect in Mn$_2$OHPO$_4$ product is the most obvious, while MnHPO$_4$ product showed partial Tyndall effect. This may be because the diameter of MnHPO$_4$ product is slightly larger than 100 nm, while the diameter of Mn$_2$OHPO$_4$ is about 10 nm.

Figure 3:
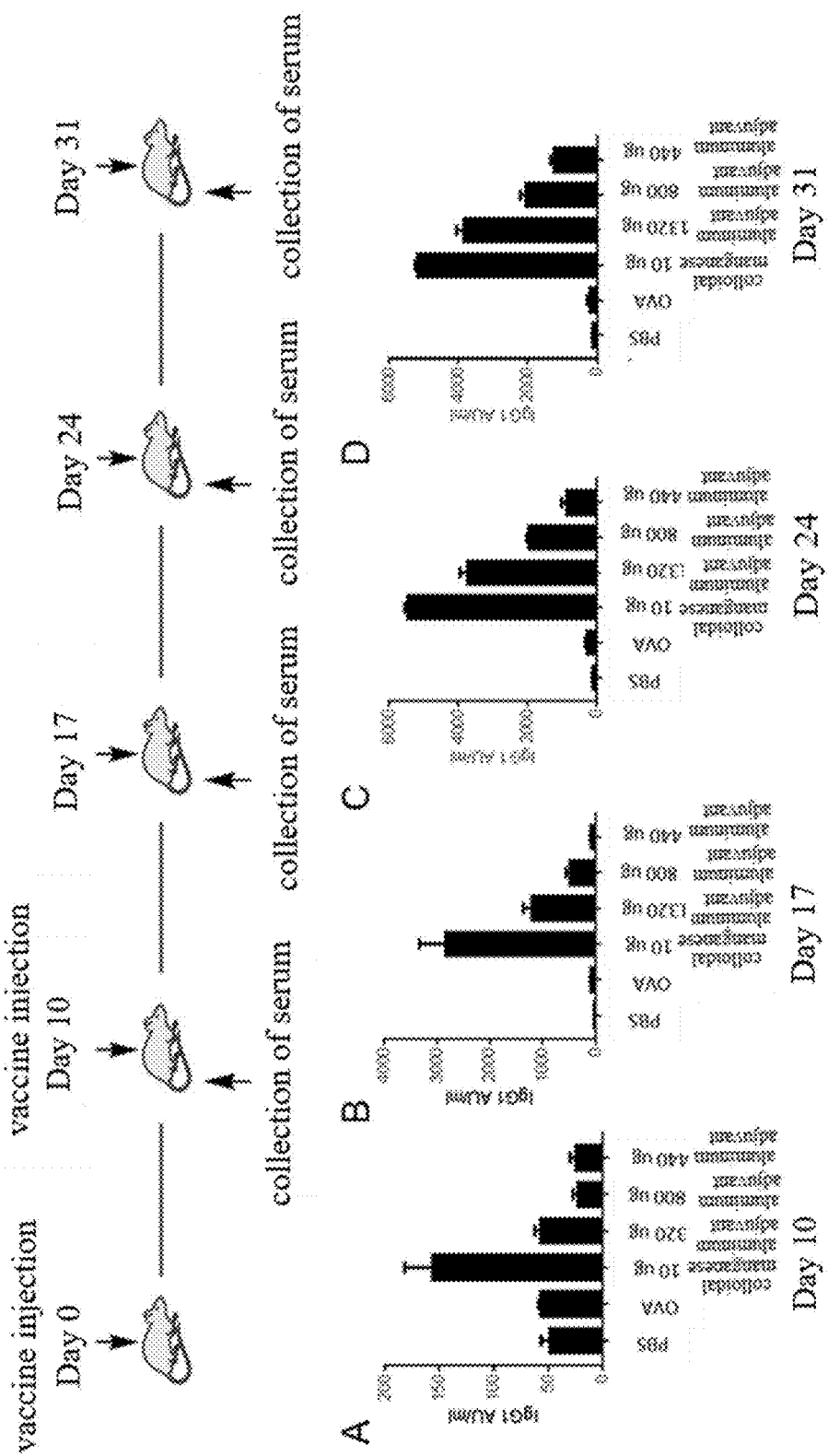
FIG. 3 illustrates the levels of anti-OVA antibodies produced 10 days (A), 17 days (B), 24 days (C) and 31 days (D) after the immunization of mice by intramuscular injection of manganese colloid ($Mn_2OHPO_4$) or aluminum adjuvant with chicken ovalbumin (OVA), respectively.

Example 3. Manganese Colloid as Adjuvant for Intramuscular Injection and Mucosal Immunization Experiment (a) Manganese Colloid (Mn$_2$OHPO$_4$) as Adjuvant for Intramuscular Injection The mice were randomly divided into 6 groups according to their body weight, namely: PBS control group, antigen OVA group (10 μg), manganese colloid Mn$_2$OHPO$_4$ group (10 μg Mn$_2$OHPO$_4$+OVA), and low-dose aluminum adjuvant group (440 μg aluminum adjuvant +OVA), medium-dose aluminum adjuvant group (800 μg aluminum adjuvant +OVA) and high-dose aluminum adjuvant group (1220 μg aluminum adjuvant +OVA). Mice in each group were immunized by intramuscular injection according to the amounts of the experimental scheme, and immunized once on Day 0 and Day 10. Blood sample was collected on Day 10, Day 17, Day 24 and Day 31, the serum was separated, and the content of the IgG1 antibody against OVA was measured by ELISA. As shown in FIG. 3, manganese colloid Mn$_2$OHPO$_4$ at a dose of 10 μg/mouse was more effective than high-dose (1220 μg/mouse) aluminum adjuvant. This indicates that manganese colloid can achieve a better effect at a dose 100 times lower than that of aluminum adjuvants, which can greatly reduce the side effects of aluminum adjuvants currently widely used.

Figure 4:
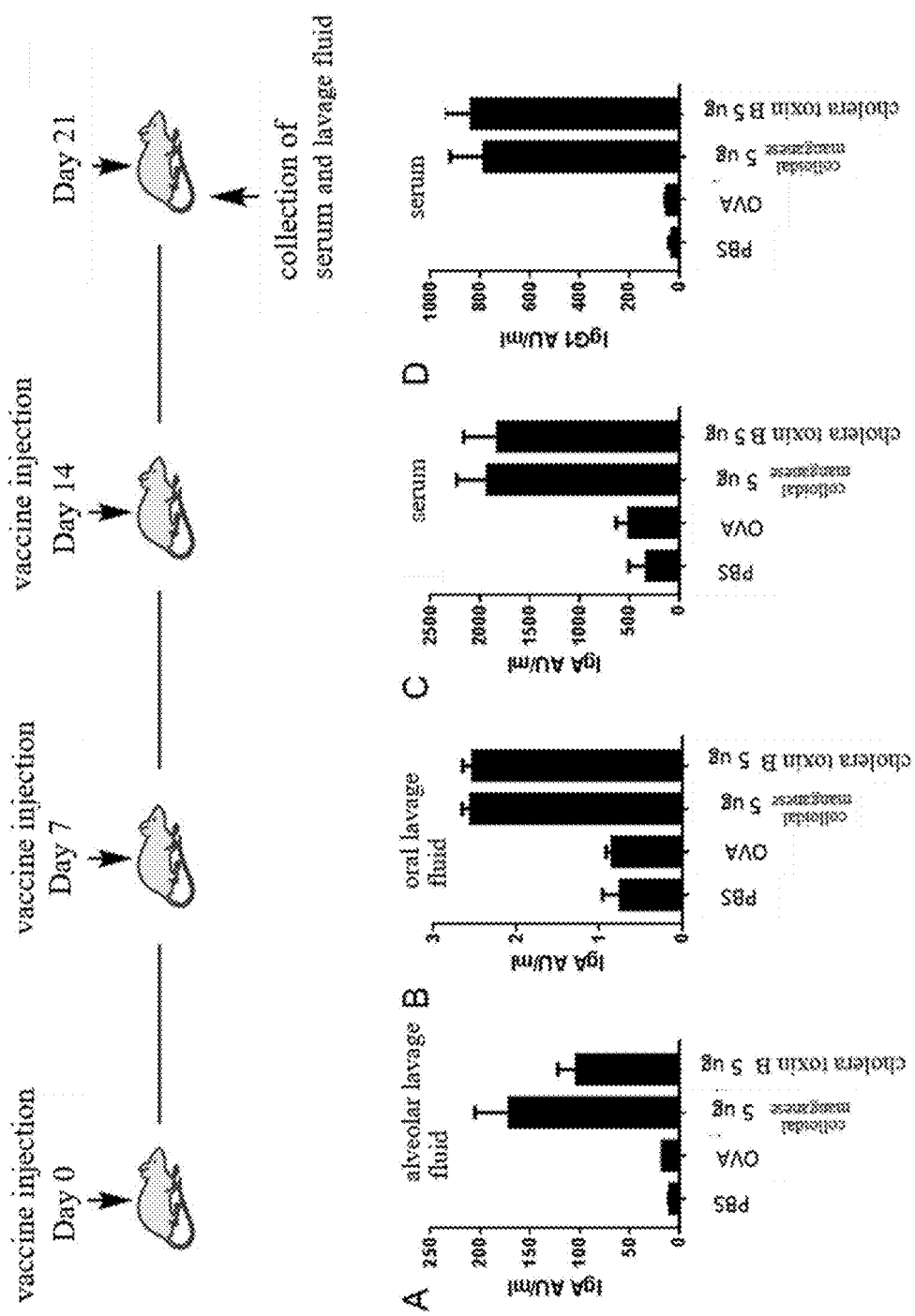
FIG. 4 shows the levels of anti-OVA antibodies in the alveolar lavage fluid (A), oral lavage fluid (B), serum IgA (C) and serum IgG1 (D) after immunizing mice through nasal drip of manganese colloid ($Mn_2OHPO_4$) or cholera toxin B (CTB) adjuvants mixed with OVA, respectively.

Experiment (b) Manganese Colloid (Mn$_2$OHPO$_4$) as Adjuvant for Mucosal Immunization As shown in FIG. 4, mice were immunized by intranasal route using the same amount (5 μg/mouse) of manganese colloid Mn$_2$OHPO$_4$ or the classical mucosal immunoadjuvant cholera toxin B (CTB), mixed with the antigen OVA (10 μg) respectively. Vaccination was performed on Day 0, Day 7 and Day 14. On Day 21, blood sample was collected to separate serum, oral lavage fluid and alveolar lavage fluid were collected, and the contents of the anti-OVA IgA antibody and IgG1 antibody were measured by ELISA. As shown in FIG. 4, when manganese colloid Mn$_2$OHPO$_4$ was used as a mucosal adjuvant, the antibody content in the alveolar lavage fluid was higher than that of cholera toxin B as the adjuvant. In oral lavage and serum, the effect of Mn$_2$OHPO$_4$ was equivalent to the same amount of cholera toxin B. This indicates that manganese colloid Mn$_2$OHPO$_4$ is also a good mucosal immunoadjuvant.

Figure 5:
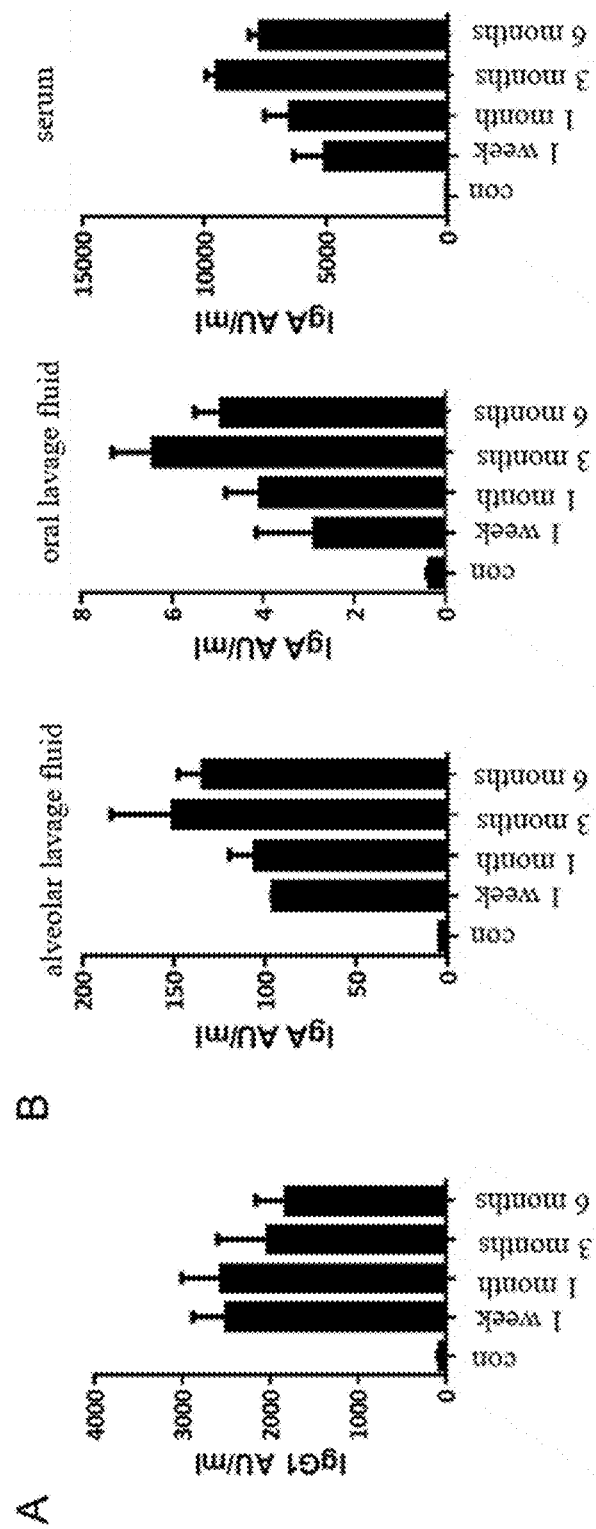
FIG. 5 illustrates the levels of anti-OVA antibodies in serum, oral lavage fluid, and alveolar lavage fluid determined for 1 to 6 months after intramuscular injection (A) or intranasal immunization (B) on mice of manganese colloid ($Mn_2OHPO_4$) as an adjuvant mixed with OVA according to the method of FIGS. 1 and 2.

Example 4. Manganese Colloid as Adjuvant for Intramuscular Injection and Mucosal Immunization Promotes Long-Term Antibody Production Experiment (a) Manganese Colloid Mn$_2$OHPO$_4$ has a Long-Lasting Effect as an Intramuscular Injection Adjuvant Using the method described in Example 3, the mice were immunized with manganese colloid Mn$_2$OHPO$_4$ as an adjuvant and mixed with OVA by intramuscular injection, and the content of the anti-OVA antibody in the serum at 1 week, 1 month, 3 months, and 6 months after immunization was determined. As shown in FIG. 5A, the anti-OVA antibody in the serum was still maintained at a high level by the sixth month, indicating that the manganese colloid $Mn_2OHPO_4$ as an adjuvant can give a lasting protection. The life span of mice is generally 2 years. It is expected that manganese colloid $Mn_2OHPO_4$ can facilitate the body to produce protective antibodies throughout the life cycle of the body.
Experiment (b) Manganese Colloid $Mn_2OHPO_4$ has a Long-Lasting Effect as a Mucosal Immunization Adjuvant Referring to the method in Example 3, after mice were immunized by intranasal route, the blood, alveolar lavage fluid, and oral lavage fluid of the mice were collected at different time points to determine the antibody content. As shown in FIG. 5B, the concentration of specific antibodies remained at a high level until 6 months after immunization, indicating that manganese colloid $Mn_2OHPO_4$ can also produce a lasting protection when used for mucosal immunization.

Example 5. Manganese (II) Activates the Production of Inflammatory Factors

The inflammatory factor IL-1β can directly act on $CD4^+$ T cells and promote the proliferation of T cells (8). IL-la and IL-1β can promote the infiltration of neutrophils (19); the inflammatory factor IL-18 can effectively enhance Th1 immune response, and can also promote the proliferation and cytotoxicity of T cells and NK cells (9). It has been reported that the adjuvant effect of aluminum adjuvant is achieved by activating NLRP3 inflammasomes and releasing inflammatory factors (20-22), so the ability of activating inflammatory factors by $MnCl_2$/manganese colloid $Mn_2OHPO_4$ or aluminum adjuvant was tested and compared.

Figure 6:
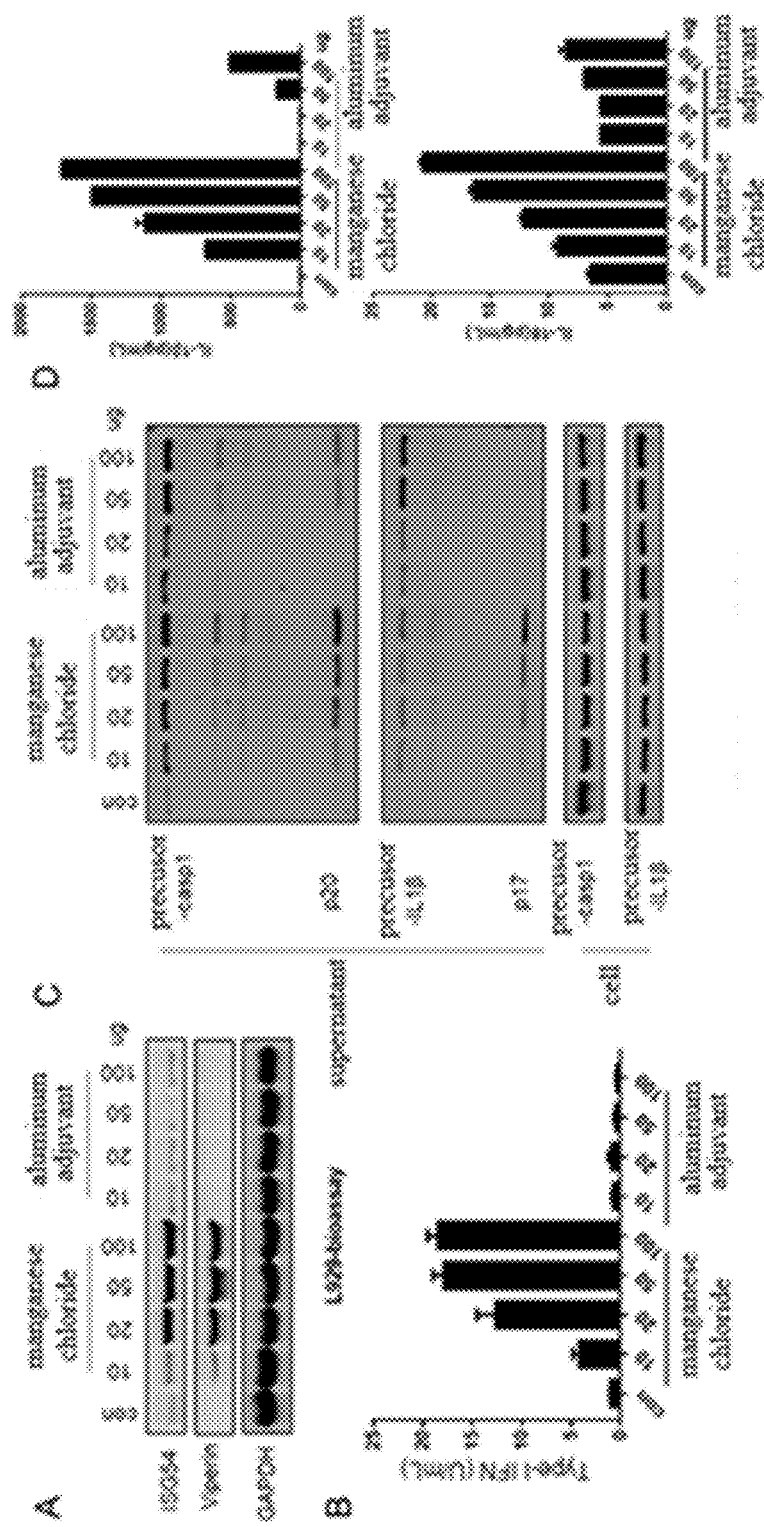
FIG. 6 illustrates the activation of type I interferon pathway and inflammasome activation by $MnCl_2$.
Figure 6:
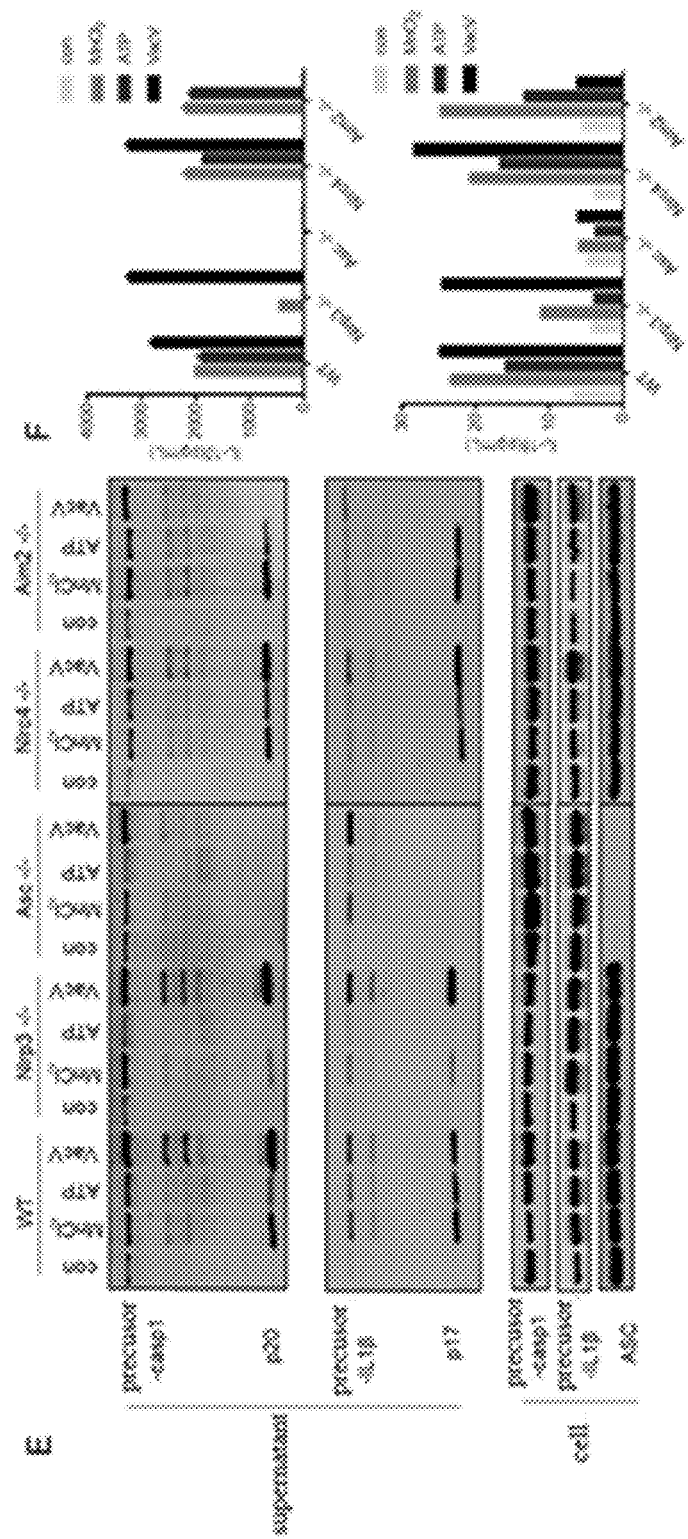

$MnCl_2$ and manganese colloid $Mn_2OHPO_4$ have the same ability to activate inflammatory factors (see FIG. 2B). Here, $MnCl_2$ is used as an example. The primary culture of mouse peritoneal macrophages in vitro was treated with 10, 20, 50, 100 μg/mL manganese chloride or aluminum adjuvant, and ISG54 and Viperin, which were induced by interferon, were detected by Western blotting. The total type I interferon content in the supernatant (the sum of the concentrations of interferon α and interferon (3) was detected by Bioassay. The results are shown in FIGS. 6A and 6B. Only $MnCl_2$ can activate the expression of type I interferon, and aluminum adjuvant cannot. The peritoneal macrophages pretreated with LPS were treated with the same concentration of manganese chloride and aluminum adjuvant, and the cleavage of caspase 1 and IL-1β in the supernatant was detected by Western blotting (the upper band is the precursor, the lower band is the active form of caspase 1 and IL-1β), and the production of inflammatory factors IL-1β and IL-18 in the supernatant was detected by ELISA. The results are shown in FIGS. 6C and 6D, the ability of $MnCl_2$ to activate inflammatory factors is significantly stronger than that of aluminum adjuvant. The peritoneal macrophages pretreated with LPS were treated with $MnCl_2$, ATP (classical NLRP3 inflammasome activator), and VacV (classical Aim2 inflammasome activator), and Western blotting was used to detect the cleavage of caspase 1 and IL-1β in the supernatant (the upper band is the precursor, and the lower band is the active form of caspase 1 and IL-1β). ELISA was used to detect the production of inflammatory factors IL-1β and IL-18 in the supernatant. The results are shown in FIGS. 6E and 6F. In the NLRP3 knockout cells, the ability of $MnCl_2$ to activate inflammatory factors was significantly lowered, indicating that $MnCl_2$ mainly activates the NLRP3 inflammasome.

Example 6. Manganese Colloid Promotes T Cell Proliferation $1\times10^6$ OT-II cells labeled with CFSE dye were injected into the tail vein of mice. One day later, the mice were immunized with OVA protein. The mice were divided into groups: PBS control group, different amounts of OVA control group (1 μg, 2 μg and 5 μg), the groups of 10 μg manganese colloid mixed with 1 μg, 2 μg, and 5 μg OVA protein respectively, and the groups of 1220 μg aluminum adjuvant mixed with 1 μg, 2 μg, and 5 μg OVA protein, respectively. The used amount described here are the amount of one immunization of one mouse. Lymph nodes were collected three days after the immunization, and the proliferation of OT-II cells in the lymph nodes was analyzed by flow cytometry.

Figure 7:
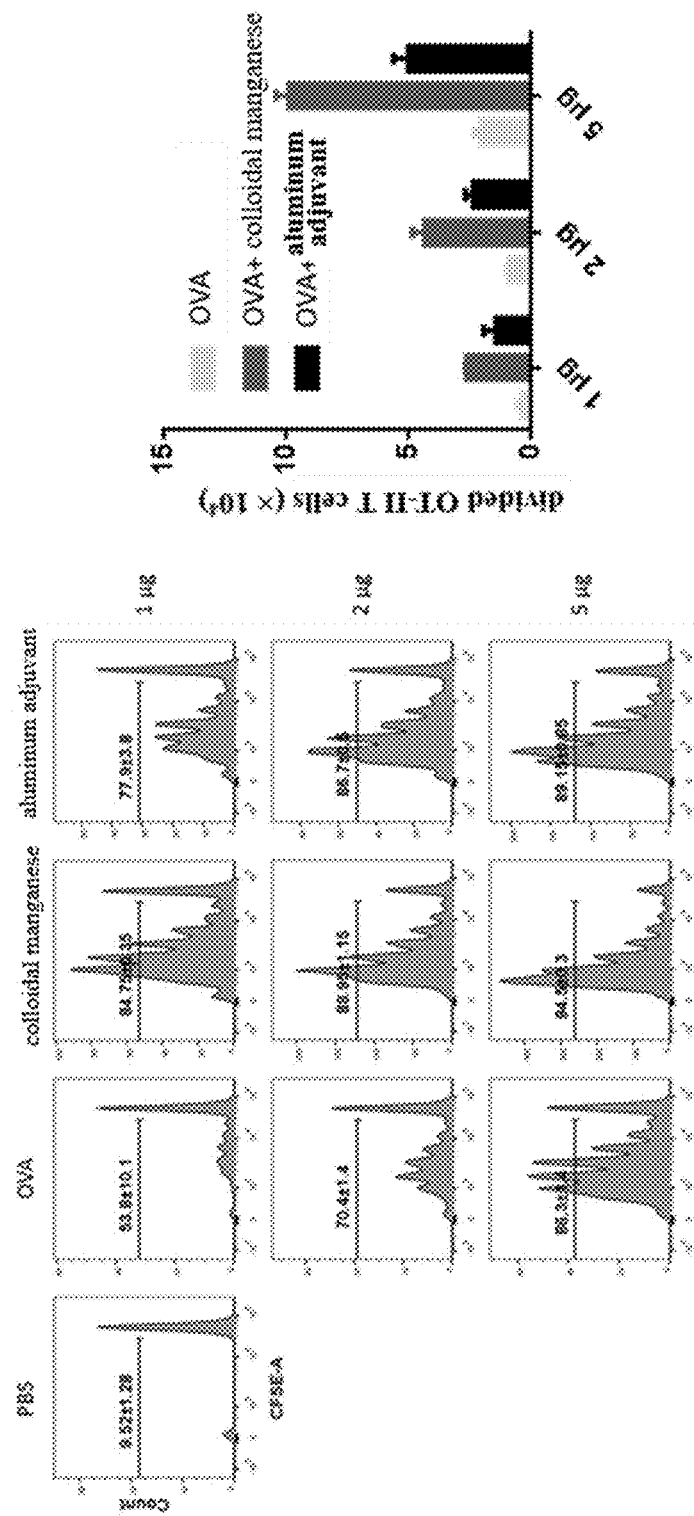
FIG. 7 illustrates that manganese colloid ($Mn_2OHPO_4$) promotes the proliferation of $CD4^+$ T cells with aluminum adjuvant as a control.

As shown in FIG. 7, the rightmost peak in each figure is the original OT-II cells injected into the mouse body. When the cell divides, the CFSE in the cell will be evenly distributed into two cells, so the brightness of the CFSE in the cell will decrease, and the cells with decreased CFSE on the left are divided cells. The results show that when the same amount of antigen is used, the ability of manganese colloid to promote T cell proliferation is stronger than that of aluminum adjuvant, and the amount of manganese colloid only needs 1/100 of that of aluminum adjuvant to achieve a similar effect.

Figure 8:
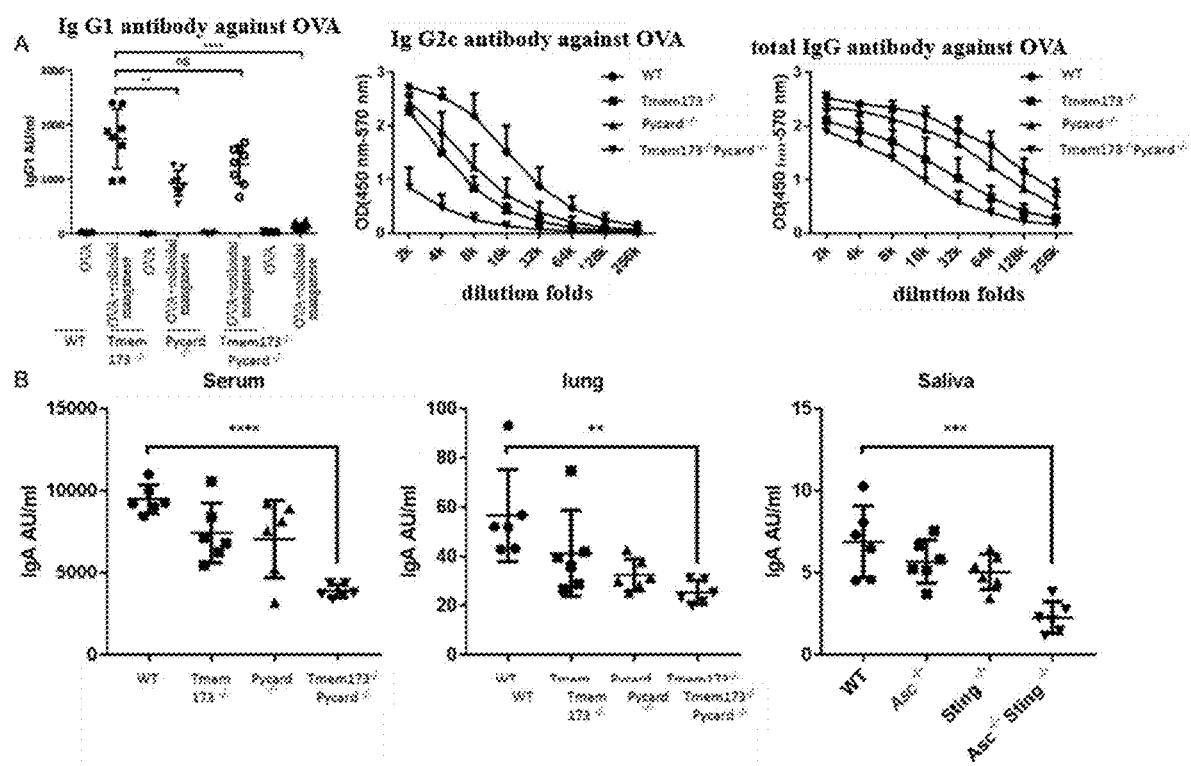
FIG. 8 illustrates that the levels of antibodies produced by mice using manganese colloid ($Mn_2OHPO_4$) as adjuvant for intramuscular injection or mucosal immunization depends on the cGAS-STING pathway and the inflammasome pathway.

Example 7. Antibody Production Activated by Manganese Colloid ($Mn_2OHPO_4$) Depends on the STING Pathway and the Inflammasome Pathway As shown in FIG. 8, FIG. 8A shows the contents of anti-OVA IgG1, IgG2c and total IgG in the mouse serum by ELISA of WT, Pycard knock-out (ASC protein deficiency), Sting knock-out (STING protein deficiency), and Pycard/Sting double-knocked mice after three intramuscular injections of 10 μg manganese colloid plus 10 μg+OVA protein per animal. The results show that in Pycard or Sting knock-out alone mice, the adjuvant effect of colloidal manganese is partially reduced, while in double knockout mice, will the adjuvant effect of manganese colloid is significantly reduced. FIG. 8B shows the secretory anti-OVA IgA antibody content in the serum, alveolar lavage fluid, and oral lavage fluid detected by ELISA after the mice were immunized via mucous membrane three times with 5 μg manganese colloid and 10 μg OVA protein per mouse. The results show that the adjuvant effect of manganese colloid was significantly reduced in double knock-out mice.

Example 8. Manganese Colloid Promotes the Maturation of Dendritic Cells

Figure 9:
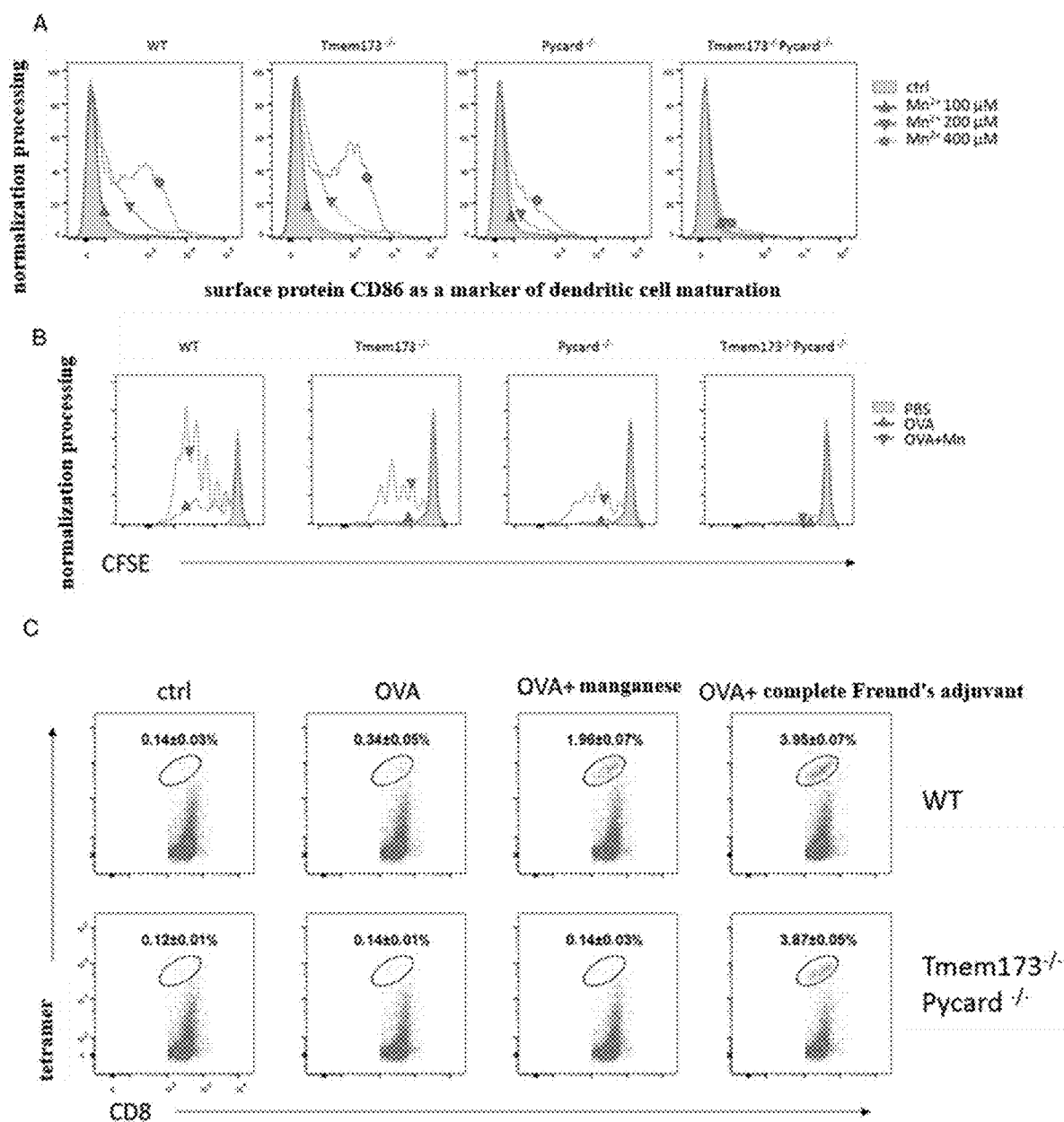
FIG. 9 illustrates that the ability of manganese colloid ($Mn_2OHPO_4$) to promote the maturation of dendritic cells and to activate T cells depends on the cGAS-STING pathway and the inflammasome pathway.

As shown in FIG. 9, FIG. 9A shows that 100, 200, and 400 μM manganese colloid ($Mn_2OHPO_4$) were used to treat bone marrow-derived dendritic cells (BMDC) for 20 hours and flow cytometry was used to detect the CD86 protein, which is a marker of dendritic cell maturation. The results showed that as the manganese colloid concentration increased in wild-type mice, it promoted the maturation of more dendritic cells. In double knock-out cells, it cannot promote cell maturation. In FIG. 9B, the method described in Example 6 was used in four kinds of mice to test the efficiency of manganese colloid in promoting T cell proliferation. The results showed that in double knock-out mice, the ability of manganese colloid as adjuvant to promote the proliferation of T cells was significantly reduced, which is also consistent with the maturation of dendritic cells. In FIG. 9C, wild-type mice and double knock-out mice were injected intramuscularly with 10 μg of manganese colloid plus 10 μg of OVA protein per mouse, and the OVA tetramer protein content on the surface of $CD8^+$ T cells was analyzed by flow cytometry (OVA-specific $CD8^+$ T cells indicating the activation of adjuvants). The results show that manganese colloid can activate the immune response of $CD8^+$ T cells, and this activation depends on the two pathways: STING and ASC.

Example 9. Manganese Colloid as Adjuvant Enhances the Immune Protection Effect of Inactivated Vesicular Stomatitis Virus (VSV) and Herpes Simplex Virus (HSV-1)

Experiment (a) VSV Inactivated Virus Vaccine

Figure 10:
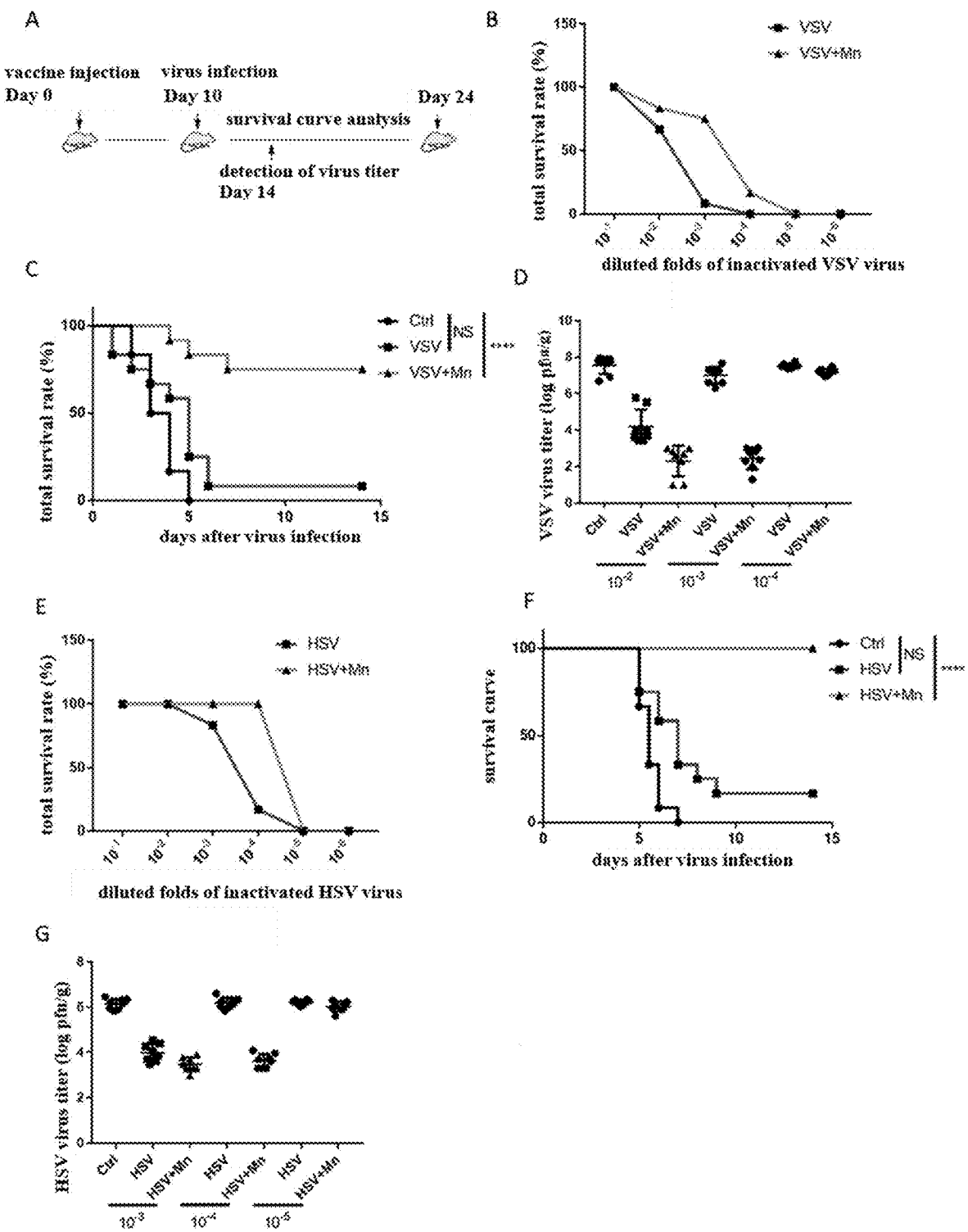
FIG. 10 shows that manganese colloid ($Mn_2OHPO_4$) as an adjuvant significantly enhances the immune protection of inactivated vesicular stomatitis virus (VSV) and herpes simplex virus (HSV-1).
Figure 11:
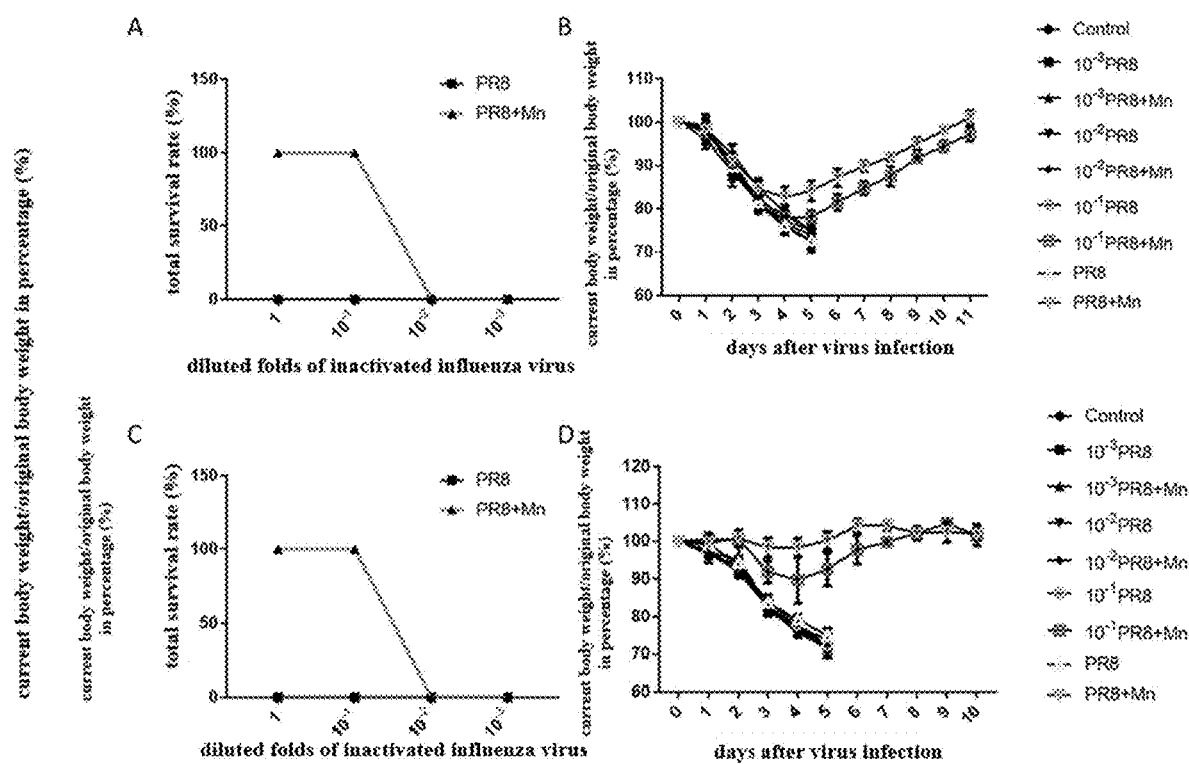
FIG. 11 shows that manganese colloid ($Mn_2OHPO_4$) as an adjuvant significantly enhances the immune protection effect of inactivated influenza virus PR8.
Figure 12:
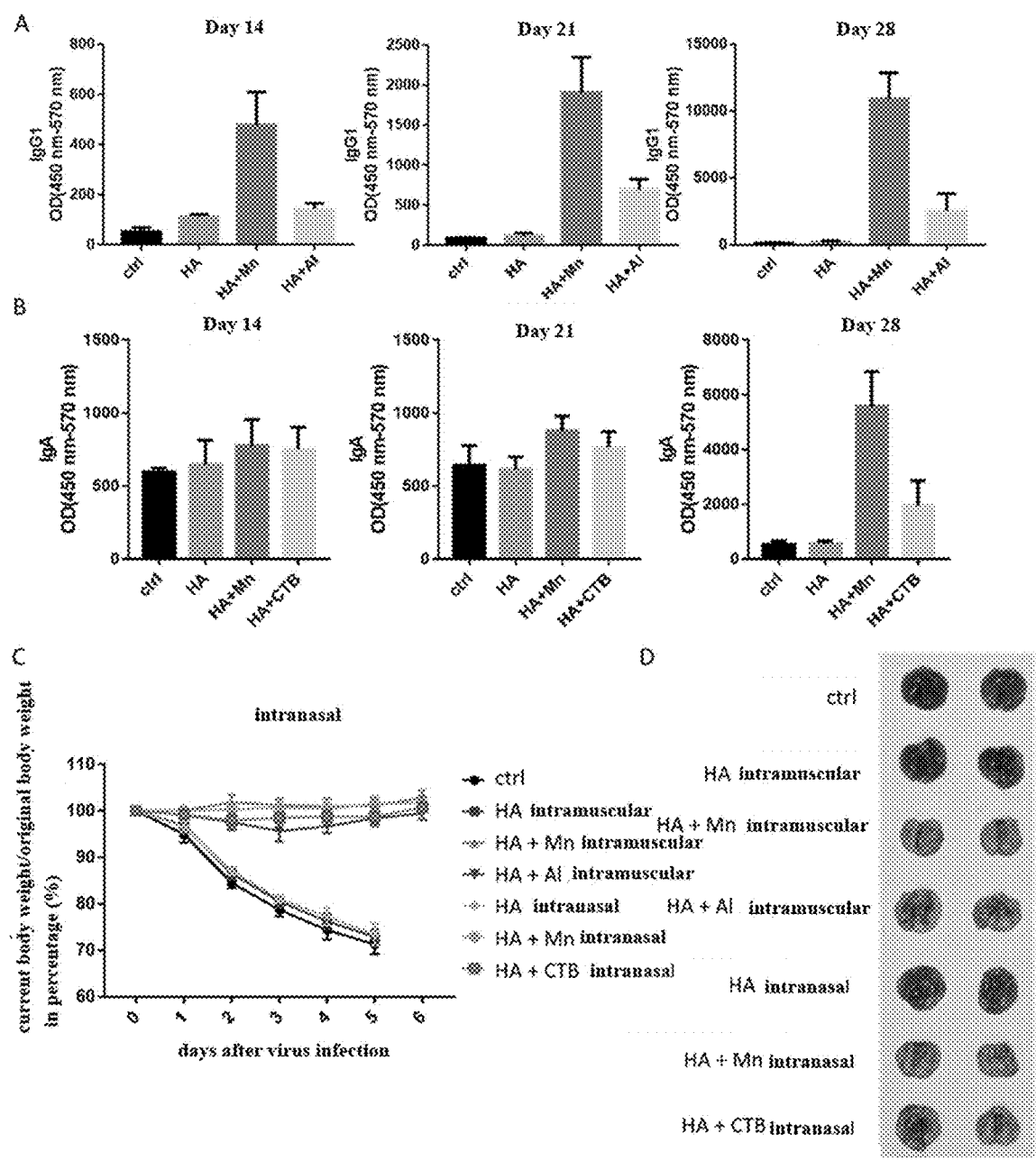
FIG. 12 illustrates that manganese colloid ($Mn_2OHPO_4$) as an adjuvant significantly enhances the immuno protection effect of influenza subunit HA vaccine.
Figure 13:
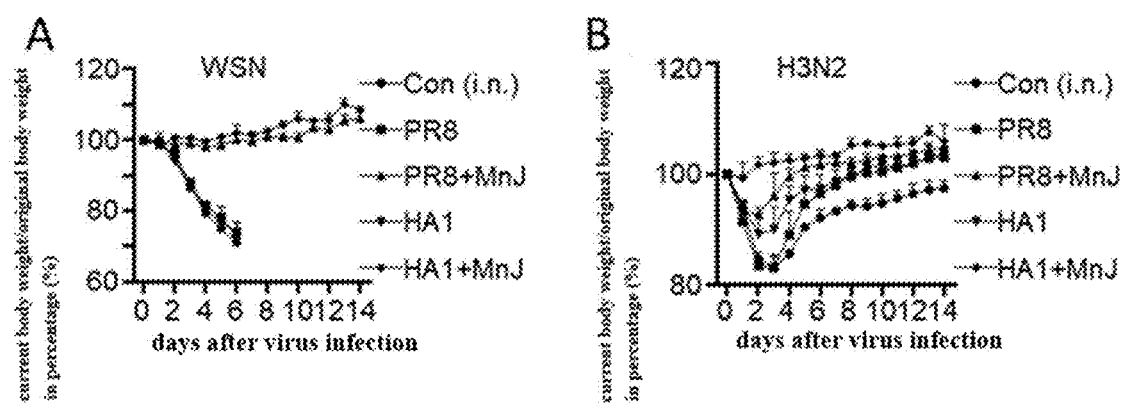
FIG. 13 illustrates the use of manganese colloid $Mn_2OHPO_4$ as an adjuvant to enhance the protection effect of inactivated influenza virus and subunit vaccines against homeotic influenza virus (WSN) and heterologous influenza virus (H3N2).

The experimental procedure is shown in FIG. 10A. On Day 0, mice were injected with vaccine intramuscularly, on Day 10, mice were infected with virus, and virus titer in mouse tissues was measured on Day 14. The mice were observed and the death curve was recorded until Day 14.

The PEG-purified VSV virus was inactivated and used as a vaccine and diluted to $10^{-1}$, $10^{-2}$, $10^{-3}$, $10^{-4}$, $10^{-5}$, and $10^{-6}$ dilutions to immunize mice by intramuscular injection. When the virus concentration is high enough, the vaccine can produce enough immune effect to protect the mice when the virus is used alone. After dilution by 10 times, when the concentration of virus was $10^{-3}$, the survival rate of mice was only 8.3%. When the concentration of virus was $10^{-4}$, $10^{-5}$, and $10^{-6}$, all mice died. But when $Mn_2OHPO_4$ colloid was added as an adjuvant to immunize mice with inactivated virus at a concentration of $10^{-3}$, the survival rate of mice increased to 75%, as shown in FIGS. 10B and 10C. It shows that manganese colloid ($Mn_2OHPO_4$) as an adjuvant can enhance the immune effect of low-concentration immunogens, so using a small amount of immunogen can give good protection, and the active virus titer in mice is also reduced, as shown in FIG. 10D.

Experiment (b) HSV-1 Inactivated Virus Vaccine

The PEG-purified HSV-1 virus was inactivated and used as a vaccine to immunize mice by intramuscular injection. When the virus dilution was $10^{-1}$ and $10^{-2}$, it could produce enough immune effect to protect mice when the virus was used alone. But when the virus dilution was reduced to $10^{-4}$, the survival rate of mice was only 16.7%, and all the mice died when the concentration was lower. While adding $Mn_2OHPO_4$ colloid to the virus at $10^{-4}$ dilution, the survival rate of mice raised to 100%, as shown in FIGS. 10E and 10F. In addition, the active virus titer in mice was reduced, as shown in FIG. 10G. This indicates that manganese colloid as an adjuvant can achieve the same protection effect while reducing the dose of inactivated HSV-1 virus by 10 times.

Experiment (c) Mucosal Immunization Once with PR8 Inactivated Virus Vaccine

The PEG-purified influenza PR8 virus was inactivated and diluted to dilutions of 1, $10^{-1}$, $10^{-2}$, and $10^{-3}$, and the mice were immunized once by intranasal route. Seven days later, the mice were infected with influenza virus, and the survival rate and weight change of the mice were recorded. All doses had no protection effect when no adjuvant was added, and the weight of the mouse dropped until death. While adding $Mn_2OHPO_4$ colloid as an adjuvant, the weight of the mouse increase after dropping in the first 4-5 days when the dilution of virus is $10^{-1}$. At Day 10, the body weight returned to the level before the virus infection, and the condition improved, as shown in FIGS. 11A and 11B. This result indicates that manganese colloid can be used as an adjuvant with an immunogen that is originally non-immunogenic or weakly immunogenic to produce a protection effect after immunizing a subject once.

Experiment (d) Mucosal Immunization Twice with PR8 Inactivated Virus Vaccine

As shown in FIGS. 11C and 11D, the PEG-purified influenza PR8 virus was inactivated and diluted to dilutions of 1, $10^{-1}$, $10^{-2}$, and $10^{-3}$, and mice were immunized via mucosal drop twice (Day 0 and Day 17). After 14 days, the mice were infected with influenza virus, and the survival rate and weight change of the mice were recorded. All doses had no protection effect when no adjuvant was added, and the weight of the mice continued to drop until death. While after the mice were immunized twice with the virus diluted to a dose of $10^{-1}$ with additional $Mn_2OHPO_4$ colloid as an adjuvant, and the weight of the mice only dropped by 10% after the mice were infected with virus, and then recovered quickly; while the mice did not lose weight after immunization with the undiluted virus, nor did they show symptoms of infection. These results showed that after the manganese colloid was added as an adjuvant to a vaccine that originally had no immune effect, a significant preventive effect was achieved after two immunizations.

Example 10. Manganese Colloid as Adjuvant Enhances the Protection Effect of Influenza Subunit Vaccine The mice were randomly divided into 4 groups according to their body weight: blank control group (ctrl), HA antigen group (HA), HA antigen and manganese colloid group (HA+Mn), and HA antigen and aluminum adjuvant group (HA+Al). After intramuscular injection, the anti-HA IgG1 antibodies in the mice serums were detected on Day 14, Day 21 and Day 28. As shown in FIG. 12A, when HA protein (5 μg/mouse) was used alone, no detectable specific antibody was produced; when $Mn_2OHPO_4$ colloid (50 μg/mouse) was added as an adjuvant, the amount of anti-HA IgG1 antibody produced after intramuscular injection immunization was significantly higher than aluminum adjuvant (800 μg/mouse). Comparing the effects of manganese colloid and CTB as an adjuvant for intranasal immunization, when $Mn_2OHPO_4$ colloid (20 μg/mouse) was added as an adjuvant, the anti-HA IgA antibody level was significantly higher than that of CTB as an adjuvant after 4 weeks of immunization (5 μg/mouse). And after the mice were immunized with manganese colloid as adjuvant, the weight of the mice did not change, and there was no inflammation in the lungs. After the mice were immunized with aluminum adjuvant and CTB as adjuvants, the mice recovered slightly after a slight weight loss. There was a small amount of inflammation in lung, as shown in FIGS. 12C and 12D. These results show that manganese colloid can be used as adjuvant for subunit vaccine, which is safer and more effective than traditional adjuvants.

Example 11. Manganese Colloid as Adjuvant Enhances Protection Effect of Inactivated Influenza Virus and Subunit Vaccines Against Homeotype Influenza Virus (WSN) and Heterologous Influenza Virus (H3N2)

Experiment (a) Inactivated PR8 Virus or PR8-HA1 Protein Vaccine Mixed with Manganese Colloid ($Mn_2OHPO_4$) Prevents WSN Virus Infection The mice were randomly divided into 5 groups according to body weight: blank control group (con), inactivated virus PR8 group, inactivated virus PR8+manganese colloid group (PR8+MnJ), PR8-HA1 protein group (HA1) and PR8-HA1 protein+manganese colloid group (HA1+MnJ). On Day 0, Day 7 and Day 14, the mice were immunized, and the mice were infected with WSN virus on Day 21. The weight of the mice was recorded for 14 consecutive days. As shown in FIG. 13A, in the experimental groups with manganese colloid, the weight of the mice did not decrease, indicating that the protection effect of the virus was excellent, and the weight of the mice without adjuvant and the blank control group decreased quickly.

Experiment (b) Inactivated PR8 Virus or PR8-HA1 Protein Vaccine Mixed with Manganese Colloid ($Mn_2OHPO_4$) Prevents H3N2 Virus Infection The mice were randomly divided into 5 groups according to their body weight: blank control group (con), inactivated virus PR8 group, inactivated virus PR8+manganese colloid group (PR8+MnJ), PR8-HA1 protein group (HA1) and PR8-HA1 protein+manganese colloid group (HA1+MnJ). On Day 0, Day 7 and Day 14, the mice were immunized, and the mice were infected with H3N2 virus on Day 21. The body weight of the mice was recorded for 14 consecutive days. As shown in FIG. 13B, H3N2 virus toxicity will not cause death of mice. In the blank control group and the inactivated virus group alone, the weight of the mice was decreased by 80% before recovering, and the weight of the mice in the HA1 group alone was decreased by 90% before recovery. In the contract, the body weight in the HA1 group with manganese colloid basically did not decrease, and in the inactivated virus group with manganese colloid, the body weight recovered after a weight loss of 5% only.

Example 12. Manganese Colloid as Immune Enhancer Enhances the Anti-Tumor Effect

Figure 14:
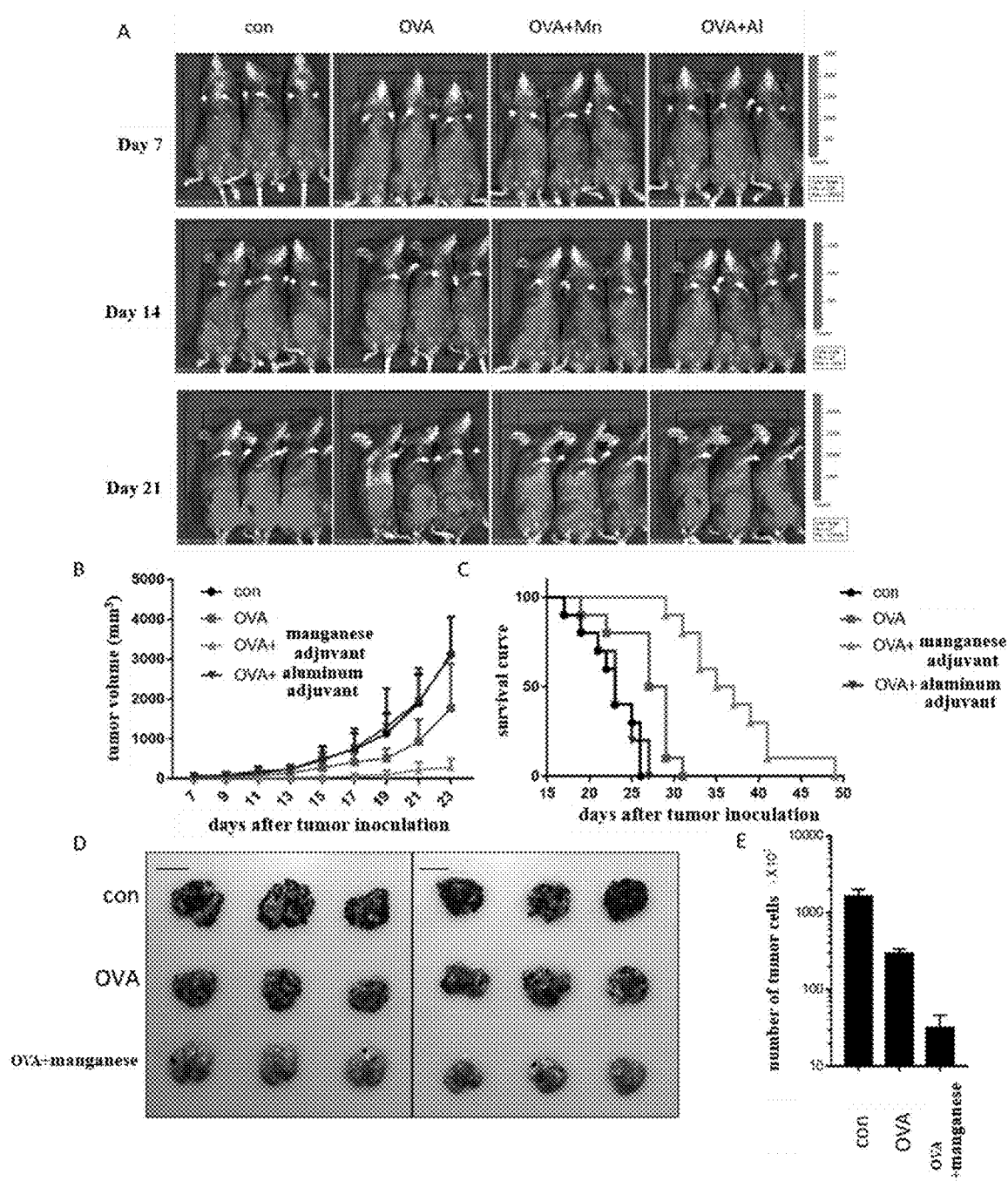
FIG. 14 illustrates that manganese colloid ($Mn_2OHPO_4$) significantly inhibits the growth of tumors in situ and metastases.

Experiment (a) Manganese Colloid $Mn_2OHPO_4$ Vaccine Inhibits Tumor Growth In Situ The mice were randomly divided into 4 groups according to body weight: blank control group (con), OVA control group, OVA and manganese colloid group (OVA+Mn), and OVA and aluminum adjuvant group (OVA+Al). After immunizing the mice three times according to the experimental scheme (once every 7 days), the B16/OVA melanoma cells were subcutaneously inoculated to establish an in situ tumor model. As shown in FIGS. 14A to 14C, the use of aluminum adjuvant in advance cannot inhibit tumor growth and improve the survival rate of mice; while the use of manganese colloid in advance can significantly inhibit tumor growth and increase the survival rate of mice. 21 days after tumor inoculation, the average tumor size of mice in the control group was 1906 $mm^3$, the average tumor size of mice in the OVA group was 925.5 $mm^3$, the average tumor size of mice immunized with manganese colloid was 222.9 $mm^3$, and the average tumor size of mice in the aluminum adjuvant group was 1946 $mm^3$, as shown in FIG. 14B. The survival time of control mice was 26 days, and the survival time of mice immunized with manganese colloid was 49 days, which was significantly longer than that of mice immunized with aluminum adjuvant, 27 days, as shown in FIG. 14C. These results indicate that manganese colloid can be used as an immune enhancer to improve the body's ability against in situ tumor.

Experiment (b) Manganese Colloid $Mn_2OHPO_4$ Vaccine Inhibits Tumor Metastasis $Mn_2OHPO_4$ colloid and aluminum adjuvant were mixed respectively with antigen OVA to immunize mice. Immunizations were performed 3 times with once every 7 days to activate the immune response in the body. B16-OVA tumor was injected into the tail vein to establish a tumor metastasis model. The mice were sacrificed 21 days after the tumor injection, and the lung tissues were taken out. It was seen that the lungs of the mice in the blank control group were covered with melanomas, and a certain number of melanomas appeared on the lungs of the mice immunized only with OVA, while there were almost no tumors on the lungs of the mice immunized with OVA+manganese colloid, as shown in FIG. 14D. After the tumor tissue was ground, the number of tumor cells was counted with a flow cytometer, which showed that the number of tumor cells in the lungs of mice immunized with OVA+manganese colloid was significantly less than the other two groups, as shown in FIG. 14E. The results indicate that manganese colloid can be used as an immune enhancer to improve the body's ability against metastatic tumors.

Figure 15:
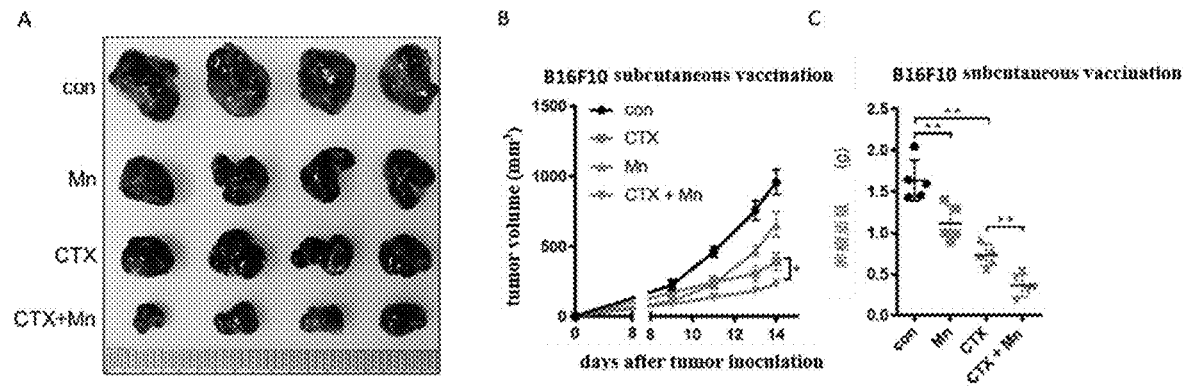
FIG. 15 illustrates the effect of manganese colloid ($Mn_2OHPO_4$) in combination with the chemotherapy drug cyclophosphamide (CTX) in the treatment of subcutaneous tumor (B16-F10 melanoma model).
Figure 16:
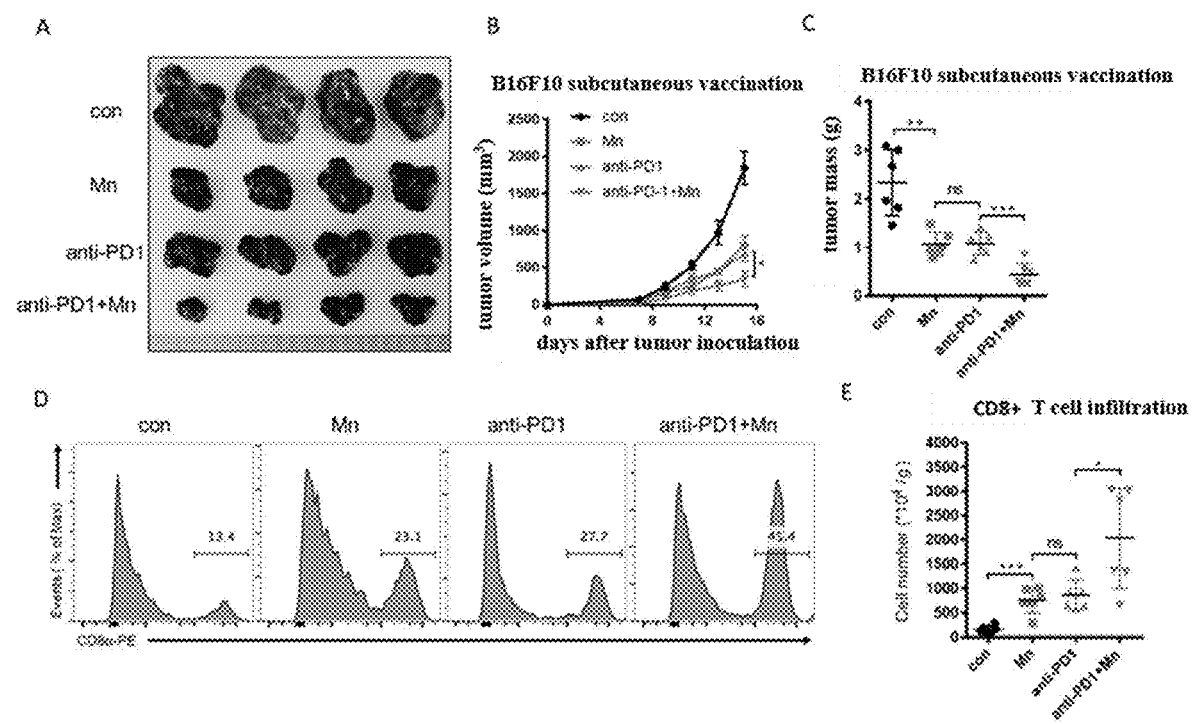
FIG. 16 illustrates the effect of manganese colloid ($Mn_2OHPO_4$) in combination with PD1 antibody drugs in the treatment of subcutaneous tumor (B16-F10 melanoma model).

Experiment (c) Manganese Colloid $Mn_2OHPO_4$ Combined with Cyclophosphamide for Anti-Tumor After subcutaneous inoculation of melanoma B16-F10 in mice, they were randomly divided into 4 groups: control group (con), $Mn_2OHPO_4$ colloid group (5 mg/kg), cyclophosphamide monohydrate (CTX) group (140 mg/kg), and the combination group (CTX+Mn). Cyclophosphamide (CTX) is a widely used anti-tumor chemotherapy drug in clinical practice. $Mn_2OHPO_4$ colloid was injected i.m. (treated once every two days after tumor inoculation), CTX was injected i.p. (treated once on the 6, 9, and 12th day after tumor inoculation), and an equal volume of normal saline was given to the control group. As shown in FIG. 15, the combination of manganese colloid and CTX can significantly inhibit tumor growth. 14 days after tumor inoculation, the mice were sacrificed, the tumors were dissected, and their volumes were measured. The average tumor size of the control group was 960.1 $mm^3$, the tumor size of mice treated with manganese colloid alone was 659.5 $mm^3$, and the tumor size of mice treated with CTX alone was 393.9 $mm^3$, and the tumor size of mice in the combination group was 238 $mm^3$, as shown in FIG. 15B. The weight of each tumor was weighed at the same time, and the results showed that the combination of manganese colloid and CTX inhibited tumor growth, as shown in FIG. 15C. This shows that manganese colloid as an immune enhancer enhances traditional treatment, such as chemotherapy, and the combination has a significant inhibitory effect on tumor growth.

Experiment (d) Manganese Colloid $Mn_2OHPO_4$ Combined with PD-1 Antibody Against Melanoma After subcutaneous inoculation of melanoma B16-F10 in mice, the mice were randomly divided into 4 groups: control group (con), $Mn_2OHPO_4$ colloid group (5 mg/kg), anti-PD1 antibody group (200 μg/mouse), and the combination group (anti-PD1+Mn). PD1 antibodies are new drugs used in immunotherapy in recent years. PD1 antibody (Clone 29 F.1A12, BioXCell) was used in treatment once on the 3rd, 7th, and 11th day after tumor inoculation, and 200 μg antibody was dissolved in 200 μl PBS for intraperitoneal injection each time. As shown in FIG. 16A-C, 15 days after tumor inoculation, the mice were sacrificed, and the tumors were dissected and measured. The average tumor size of mice in the control group was 1847 $mm^3$, and the average tumor size of mice in the manganese colloid group alone was 797.3 $mm^3$. The average tumor size of mice in the PD1 antibody group was 687.3 $mm^3$, while the average tumor size of mice in the combination treatment group was 342 mm³, which was significantly lower than that of PD1 antibody alone. Flow cytometry was used to analyze the proportion of CD8⁺ T cells infiltrated in the tumors. Manganese colloid increased the effect of the PD1 antibody drug from 27.7% to 45.4%. This indicates that manganese colloid can act synergistically with PD1 antibody drugs in treating melanoma.

Figure 17:
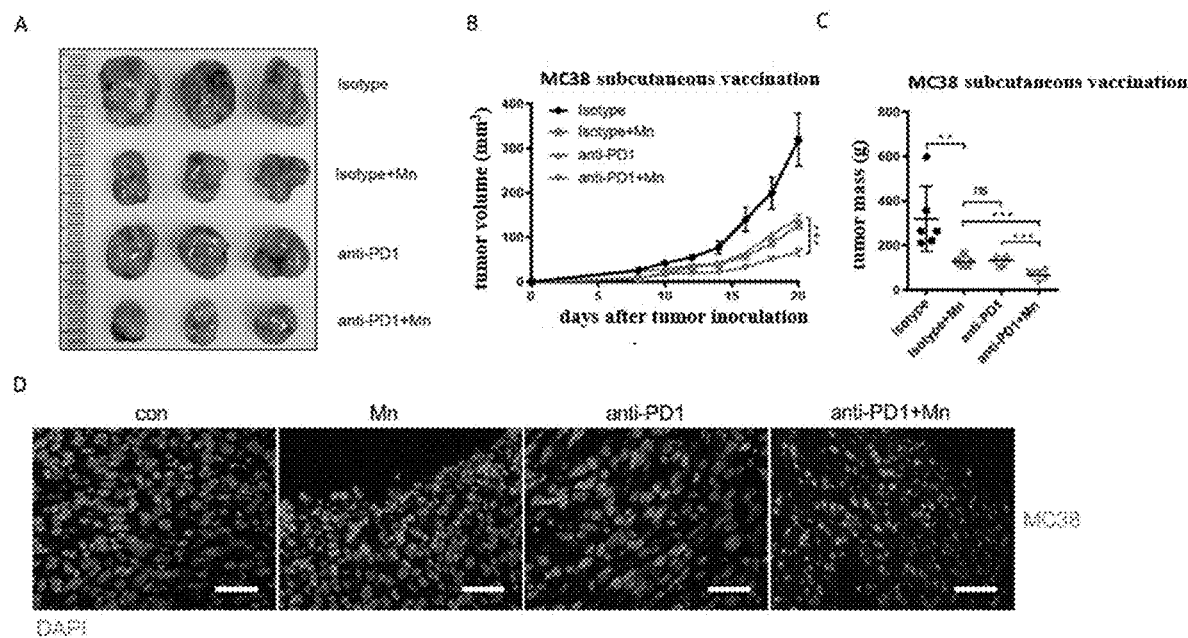
FIG. 17 illustrates the effect of manganese colloid ($Mn_2OHPO_4$) in combination with PD1 antibody drug in the treatment of subcutaneous tumor (MC38 colon cancer model).

Experiment (e) Combination of Manganese Colloid $Mn_2OHPO_4$ and PD-1 Antibody Against Colon Cancer Mice were subcutaneously inoculated with colon cancer MC38 cells and randomly divided into 4 groups: control antibody group (Isotype, 200 μg/mouse), $Mn_2OHPO_4$ colloid and control antibody group (Isotype+Mn), anti-PD1 antibody group (200 μg/mouse) and the combination group (anti-PD1+Mn). The use of PD-1 antibody was the same as in experiment (d). Twenty days after inoculation, the mice were sacrificed and the tumors were dissected and measured. The average tumor size of mice in the control group was 319.8 mm³, the tumor size of mice treated with manganese alone was 126.9 mm³, and the tumor size of mice treated with PD1 antibody drug alone was 143.1 mm³. The tumor size of the combined treatment group was 66.74 mm³, as shown in FIG. 17B. The tumor tissue sections were subjected to immunofluorescence staining of DAPI and CD8⁺ T cells. It can be seen that the proportion of CD8⁺ T cells infiltrated in the tumor of mice treated with the combination of PD1 antibody and manganese colloid was significantly increased, as shown in FIG. 17D. This indicates that manganese colloid can act synergistically with PD1 antibody drugs in treating colon cancer.

REFERENCES

1. S. Akira, K. Takeda, Toll-like receptor signalling. *Nature reviews. Immunology* 4, 499-511 (2004); published online EpubJul (10.1038/nri1391).
2. A. M. Bruns, C. M. Horvath, Activation of RIG-I-like receptor signal transduction. *Critical reviews in biochemistry and molecular biology* 47, 194-206 (2012); published online EpubMar-Apr (10.3109/10409238.2011.630974).
3. Z. Ma, B. Damania, The cGAS-STING Defense Pathway and Its Counteraction by Viruses. *Cell Host Microbe* 19, 150-158 (2016); published online EpubFeb 10 (10.1016/j.chom.2016.01.010).
4. K. Schroder, J. Tschopp, The inflammasomes. *Cell* 140, 821-832 (2010); published online EpubMar 19 (10.1016/j.cell.2010.01.040).
5. L. B. Ivashkiv, L. T. Donlin, Regulation of type I interferon responses. *Nature reviews. Immunology* 14, 36-49 (2014); published online EpubJan (10.1038/nri3581).
6. W. M. Schneider, M. D. Chevillotte, C. M. Rice, Interferon-stimulated genes: a complex web of host defenses. *Annu Rev Immunol* 32, 513-545 (2014)10.1146/annurev-immunol-032713-120231).
7. M. P. Longhi, C. Trumpfheller, J. Idoyaga, M. Caskey, I. Matos, C. Kluger, A. M. Salazar, M. Colonna, R. M. Steinman, Dendritic cells require a systemic type I interferon response to mature and induce CD4+ Th1 immunity with poly IC as adjuvant. *The Journal of experimental medicine* 206, 1589-1602 (2009); published online EpubJul 6 (10.1084/jem.20090247).
8. S. Z. Ben-Sasson, J. Hu-Li, J. Quiel, S. Cauchetaux, M. Ratner, I. Shapira, C. A. Dinarello, W. E. Paul, IL-1 acts directly on CD4 T cells to enhance their antigen-driven expansion and differentiation. *Proceedings of the National Academy of Sciences of the United States of America* 106, 7119-7124 (2009); published online EpubApr 28 (10.1073/pnas.0902745106).
9. N. S. Wilson, P. Duewell, B. Yang, Y. Li, S. Marsters, S. Koernig, E. Latz, E. Maraskovsky, A. B. Morelli, M. Schnurr, A. Ashkenazi, Inflammasome-dependent and -independent IL-18 production mediates immunity to the ISCOMATRIX adjuvant. *Journal of immunology* 192, 3259-3268 (2014); published online EpubApr 1 (10.4049/jimmunol.1302011).
10. P. Marrack, A. S. McKee, M. W. Munks, Towards an understanding of the adjuvant action of aluminium. *Nature reviews. Immunology* 9, 287-293 (2009); published online EpubApr (10.1038/nri2510).
11. H. Nohynek, J. Jokinen, M. Partinen, O. Vaarala, T. Kirjavainen, J. Sundman, S. L. Himanen, C. Hublin, I. Julkunen, P. Olsen, O. Saarenpaa-Heikkila, T. Kilpi, AS03 adjuvanted AH1N1 vaccine associated with an abrupt increase in the incidence of childhood narcolepsy in Finland. *PloS one* 7, e33536 (2012)10.1371/journal.pone.0033536).
12. C. K. Tang, T. Aoshi, N. Jounai, J. Ito, K. Ohata, K. Kobiyama, B. H. Dessailly, E. Kuroda, S. Akira, K. Mizuguchi, C. Coban, K. J. Ishii, The chemotherapeutic agent DMXAA as a unique IRF3-dependent type-2 vaccine adjuvant. *PloS one* 8, e60038 (2013)10.1371/journal.pone.0060038).
13. S. M. Blaauboer, V. D. Gabrielle, L. Jin, MPYS/STING-mediated TNF-alpha, not type I IFN, is essential for the mucosal adjuvant activity of (3'-5')-cyclic-di-guanosine-monophosphate in vivo. *Journal of immunology* 192, 492-502 (2014); published online EpubJan 01 (10.4049/jimmunol.1301812).
14. X. D. Li, J. Wu, D. Gao, H. Wang, L. Sun, Z. J. Chen, Pivotal roles of cGAS-cGAMP signaling in antiviral defense and immunoadjuvant effects. *Science* 341, 1390-1394 (2013); published online EpubSep 20 (10.1126/science.1244040).
15. E. C. Carroll, L. Jin, A. Mori, N. Munoz-Wolf, E. Oleszycka, H. B. Moran, S. Mansouri, C. P. McEntee, E. Lambe, E. M. Agger, P. Andersen, C. Cunningham, P. Hertzog, K. A. Fitzgerald, A. G. Bowie, E. C. Lavelle, The Vaccine Adjuvant Chitosan Promotes Cellular Immunity via DNA Sensor cGAS-STING-Dependent Induction of Type I Interferons. *Immunity* 44, 597-608 (2016); published online EpubMar 15 (10.1016/j.immuni.2016.02.004).
16. C. Wang, Y. Guan, M. Lv, R. Zhang, Z. Guo, X. Wei, X. Du, J. Yang, T. Li, Y. Wan, X. Su, X. Huang, Z. Jiang, Manganese Increases the Sensitivity of the cGAS-STING Pathway for Double-Stranded DNA and Is Required for the Host Defense against DNA Viruses. *Immunity* 48, 675-687 e677 (2018); published online EpubApr 17 (10.1016/j.immuni.2018.03.017).
17. Z. Jiang, P. Georgel, X. Du, L. Shamel, S. Sovath, S. Mudd, M. Huber, C. Kalis, S. Keck, C. Galanos, M. Freudenberg, B. Beutler, CD14 is required for MyD88-independent LPS signaling. *Nature immunology* 6, 565-570 (2005); published online EpubJun (10.1038/ni1207).
18. Y. Xia, Y. Xie, Z. Yu, H. Xiao, G. Jiang, X. Zhou, Y. Yang, X. Li, M. Zhao, L. Li, M. Zheng, S. Han, Z. Zong, X. Meng, H. Deng, H. Ye, Y. Fa, H. Wu, E. Oldfield, X. Hu, W. Liu, Y. Shi, Y. Zhang, The Mevalonate Pathway Is a Druggable Target for Vaccine Adjuvant Discovery. *Cell* 175, 1059-1073 e1021 (2018); published online EpubNov 1 (10.1016/j.cell.2018.08.070).

19. E. Oleszycka, H. B. Moran, G. A. Tynan, C. H. Hearnden, G. Coutts, M. Campbell, S. M. Allan, C. J. Scott, E. C. Lavelle, IL-1alpha and inflammasome-independent IL-1beta promote neutrophil infiltration following alum vaccination. *FEBS J* 283, 9-24 (2016); published online EpubJan (10.1111/febs.13546).

20. S. C. Eisenbarth, O. R. Colegio, W. O'Connor, F. S. Sutterwala, R. A. Flavell, Crucial role for the Nalp3 inflammasome in the immunostimulatory properties of aluminium adjuvants. *Nature* 453, 1122-1126 (2008); published online EpubJun 19 (10.1038/nature06939).

21. M. Kool, V. Petrilli, T. De Smedt, A. Rolaz, H. Hammad, M. van Nimwegen, I. M. Bergen, R. Castillo, B. N. Lambrecht, J. Tschopp, Cutting Edge: Alum Adjuvant Stimulates Inflammatory Dendritic Cells through Activation of the NALP3 Inflammasome. *The Journal of Immunology* 181, 3755-3759 (2008)10.4049/jimmunol.181.6.3755).

22. H. Li, S. B. Willingham, J. P. Y. Ting, F. Re, Cutting Edge: Inflammasome Activation by Alum and Alum's Adjuvant Effect Are Mediated by NLRP3. *The Journal of Immunology* 181, 17-21 (2008)10.4049/jimmunol.181.1.17).

The invention claimed is:

1. A composition for enhancing immunity, comprising a manganese colloid, wherein the manganese colloid is $Mn_2OHPO_4$ colloid.

2. A vaccine composition, comprising
A) vaccine immunogen, and
B) manganese colloid according to claim 1;
wherein component A and component B are in the same or separate containers.

3. The vaccine composition according to claim 2, wherein the vaccine immunogen is derived from a virus, a bacterium and/or a parasite.

4. An immunoadjuvant comprising the composition for enhancing immunity according to claim 1.

5. A method for enhancing immunity, which comprises administering the composition for enhancing immunity according to claim 1 to a subject in need thereof,
wherein, the immune enhancement is,
A) to improve innate immunity and/or adaptive immunity,
B) to increase expression of type I interferon,
C) to induce production of inflammatory factors in active form,
D) to promote antibody production,
E) to promote proliferation of T cells, and/or
F) to promote maturation of dendritic cells.

6. The method according to claim 5, wherein the administration is selected from the group consisting of intramuscular injection, intradermal injection, subcutaneous injection, intravenous injection, mucosal administration, and a combination thereof.

7. The method according to claim 5, wherein the enhancing immunity is used to prevent and/or treat diseases selected from the group consisting of bacterial infections, fungal infections, viral infections, parasitic infections, tumors, and autoimmune diseases.

8. The method according to claim 7, wherein the virus is selected from the group consisting of Herpesviridae, Rhabdoviridae, Filoviridae, Orthomyxoviridae, Paramyxoviridae, Coronaviridae, Picornaviridae, Hepatoviridae, Flaviviridae, Papillomaviridae, Poxviridae, and Retroviridae.

9. The method according to claim 7, wherein the bacterium is selected from the group consisting of *Streptococcus pneumoniae, Haemophilus influenzae, Salmonella,* Meningococcus, *Staphylococcus epidermidis, Staphylococcus aureus, Escherichia coli, Klebsiella pneumoniae, Klebsiella oxytoca, Enterobacter cloacae, Citrobacter freundii, Pseudomonas aeruginosa, Acinetobacter baumanni,* tetanus *bacillus,* pertussis *bacillus,* diphtheria *bacillus,* leprosy *bacillus,* tuberculosis *bacillus,* meningococcus, pneumococcus and a combination thereof.

10. The method according to claim 7, wherein the autoimmune disease is selected from the group consisting of type I diabetes, psoriasis, rheumatoid arthritis, systemic lupus erythematosus and multiple sclerosis.

11. The method according to claim 7, wherein the tumor is selected from the group consisting of ovarian cancer, lung cancer, gastric cancer, breast cancer, liver cancer, pancreatic cancer, skin cancer, malignant melanoma, head and neck cancer, sarcoma, bile duct cancer, bladder cancer, kidney cancer, colon cancer, placental choriocarcinoma, cervical cancer, testicular cancer, uterine cancer and leukemia.

12. The method according to claim 7, wherein the parasite is an intracellular parasite selected from the group consisting of *Plasmodium, Toxoplasma, Trypanosoma, Schistosoma,* Filaria, and *Leishmania.*

13. An immunization method, comprising
administering the vaccine composition according to claim 2 to a subject in need thereof, wherein components A and B are administered at the same time or at different times when they are in different containers.

* * * * *